United States Patent
Marella

(10) Patent No.: US 7,236,847 B2
(45) Date of Patent: Jun. 26, 2007

(54) SYSTEMS AND METHODS FOR CLOSED LOOP DEFECT REDUCTION

(75) Inventor: Paul Frank Marella, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 568 days.

(21) Appl. No.: 10/342,819

(22) Filed: Jan. 15, 2003

(65) Prior Publication Data

US 2003/0139838 A1 Jul. 24, 2003

Related U.S. Application Data

(60) Provisional application No. 60/349,323, filed on Jan. 16, 2002.

(51) Int. Cl.
  G06F 17/50 (2006.01)
  H01L 21/00 (2006.01)
(52) U.S. Cl. .............. 700/110; 205/82; 438/4; 438/12; 702/35; 716/4
(58) Field of Classification Search .............. 438/4, 438/5, 12; 700/110; 702/35, 83, 108; 356/237.2; 382/149; 205/80; 716/4
See application file for complete search history.

(56) References Cited

U.S. PATENT DOCUMENTS

| | | | |
|---|---|---|---|
| 4,247,203 A | 1/1981 | Levy et al. | |
| 4,347,001 A | 8/1982 | Levy et al. | |
| 4,378,159 A | 3/1983 | Galbraith | |
| 4,448,532 A | 5/1984 | Joseph et al. | |
| 4,532,650 A | 7/1985 | Wihl et al. | |
| 4,555,798 A | 11/1985 | Broadbent, Jr. et al. | |

(Continued)

FOREIGN PATENT DOCUMENTS

EP 0 993 019 4/2000

(Continued)

OTHER PUBLICATIONS

Genut et al., "Chemically Assisted Laser Removal of Photoresist and Particles from Semiconductor Wafers," Meeting of the Fine Particle Society, Apr. 1988, 10 pages.

(Continued)

*Primary Examiner*—Leo Picard
*Assistant Examiner*—Sheela S. Rao
(74) *Attorney, Agent, or Firm*—Baker & McKenzie LLP

(57) ABSTRACT

Systems and methods for repairing defects on a specimen are provided. A method may include processing a specimen, detecting defects on the specimen, and repairing one or more of the defects. An additional method may include detecting defects on a specimen, repairing one or more of the defects, and inspecting the specimen to detect defects remaining on the specimen subsequent to repair. A system may include a process chamber, a measurement device configured to detect defects on a specimen, and a repair tool configured to repair one or more of the defects detected on the specimen. An additional system may include a measurement device, a repair tool, and an inspection tool configured to detect defects remaining on the specimen subsequent to repair. The systems may also include a processor configured to alter a parameter of an instrument coupled to the repair tool in response to output from the measurement device.

56 Claims, 9 Drawing Sheets

U.S. PATENT DOCUMENTS

| | | |
|---|---|---|
| 4,556,317 A | 12/1985 | Sandland et al. |
| 4,579,455 A | 4/1986 | Levy et al. |
| 4,601,576 A | 7/1986 | Galbraith |
| 4,618,938 A | 10/1986 | Sandland et al. |
| 4,633,504 A | 12/1986 | Wihl |
| 4,641,967 A | 2/1987 | Pecen |
| 4,644,172 A | 2/1987 | Sandland et al. |
| 4,766,324 A | 8/1988 | Saadat et al. |
| 4,805,123 A | 2/1989 | Specht et al. |
| 4,818,110 A | 4/1989 | Davidson |
| 4,845,558 A | 7/1989 | Tsai et al. |
| 4,877,326 A | 10/1989 | Chadwick et al. |
| 4,898,471 A | 2/1990 | Stonestrom et al. |
| 4,926,489 A | 5/1990 | Danielson et al. |
| 4,928,010 A | 5/1990 | Saito et al. |
| 5,023,424 A | 6/1991 | Vaught |
| 5,076,692 A | 12/1991 | Neukermans et al. |
| 5,189,481 A | 2/1993 | Jann et al. |
| 5,241,176 A | 8/1993 | Yonezawa |
| 5,264,912 A | 11/1993 | Vaught et al. |
| 5,293,216 A | 3/1994 | Moslehi |
| 5,355,212 A | 10/1994 | Wells et al. |
| 5,502,306 A | 3/1996 | Meisburger et al. |
| 5,537,669 A | 7/1996 | Evans et al. |
| 5,563,702 A | 10/1996 | Emery et al. |
| 5,565,979 A | 10/1996 | Gross |
| 5,572,598 A | 11/1996 | Wihl et al. |
| 5,578,821 A | 11/1996 | Meisberger et al. |
| 5,604,585 A | 2/1997 | Johnson et al. |
| 5,633,747 A | 5/1997 | Nikoonahad |
| 5,665,968 A | 9/1997 | Meisburger et al. |
| 5,717,204 A | 2/1998 | Meisburger et al. |
| 5,737,072 A | 4/1998 | Emery et al. |
| 5,798,829 A | 8/1998 | Vaez-Iravani |
| 5,801,965 A | 9/1998 | Takagi et al. |
| 5,822,055 A | 10/1998 | Tsai et al. |
| 5,825,482 A | 10/1998 | Nikoonahad et al. |
| 5,864,394 A | 1/1999 | Jordan, III et al. |
| 5,869,833 A | 2/1999 | Richardson et al. |
| 5,872,358 A | 2/1999 | Todokoro et al. |
| 5,883,710 A | 3/1999 | Nikoonahad et al. |
| 5,917,588 A | 6/1999 | Addiego |
| 5,973,323 A | 10/1999 | Adler et al. |
| 5,991,699 A * | 11/1999 | Kulkarni et al. ............... 702/83 |
| 6,020,214 A | 2/2000 | Watanabe et al. |
| 6,020,957 A | 2/2000 | Rosengaus et al. |
| 6,052,478 A | 4/2000 | Wihl et al. |
| 6,064,517 A | 5/2000 | Chuang et al. |
| 6,078,386 A | 6/2000 | Tsai et al. |
| 6,081,325 A | 6/2000 | Leslie et al. |
| 6,122,046 A | 9/2000 | Almogy |
| 6,175,645 B1 | 1/2001 | Elyasaf et al. |
| 6,178,257 B1 | 1/2001 | Alumot et al. |
| 6,201,998 B1 | 3/2001 | Lin et al. |
| 6,201,999 B1 | 3/2001 | Jevtic |
| 6,205,239 B1 * | 3/2001 | Lin et al. ..................... 382/149 |
| 6,215,551 B1 | 4/2001 | Nikoonahad et al. |
| 6,224,638 B1 | 5/2001 | Jevtic et al. |
| 6,242,273 B1 | 6/2001 | Goodwin et al. |
| 6,483,938 B1 | 11/2002 | Hennessey et al. |
| 6,542,830 B1 * | 4/2003 | Mizuno et al. ................ 702/35 |
| 6,797,526 B2 * | 9/2004 | Tanaka et al. .................. 438/5 |
| 6,919,957 B2 * | 7/2005 | Nikoonahad et al. .... 356/237.2 |
| 6,946,394 B2 * | 9/2005 | Fielden et al. .............. 438/680 |
| 6,949,177 B2 * | 9/2005 | Jeong .......................... 205/80 |
| 2004/0101981 A1 * | 5/2004 | Morishita ...................... 438/5 |

FOREIGN PATENT DOCUMENTS

| | | |
|---|---|---|
| EP | 1 061 358 | 12/2000 |
| EP | 1 061 571 | 12/2000 |
| EP | 1 069 609 | 1/2001 |
| EP | 1 081 489 | 3/2001 |
| EP | 1 081 742 | 3/2001 |
| EP | 1 093 017 | 4/2001 |
| WO | 98/54632 | 12/1998 |
| WO | WO 99/65056 | 12/1999 |
| WO | 00/36525 | 6/2000 |
| WO | 00/68673 | 11/2000 |
| WO | 00/70332 | 11/2000 |
| WO | 01/03145 | 1/2001 |
| WO | 01/13098 | 2/2001 |
| WO | WO 01/80304 | 12/2001 |

OTHER PUBLICATIONS

Silverman, "Laser microchemical technology enables real-time editing a first-run silicon," Solid State Technology, Sep. 1996, 4 pages.

International Search Report, application No. PCT/US 03/01419, mailed Feb. 17, 2004.

* cited by examiner

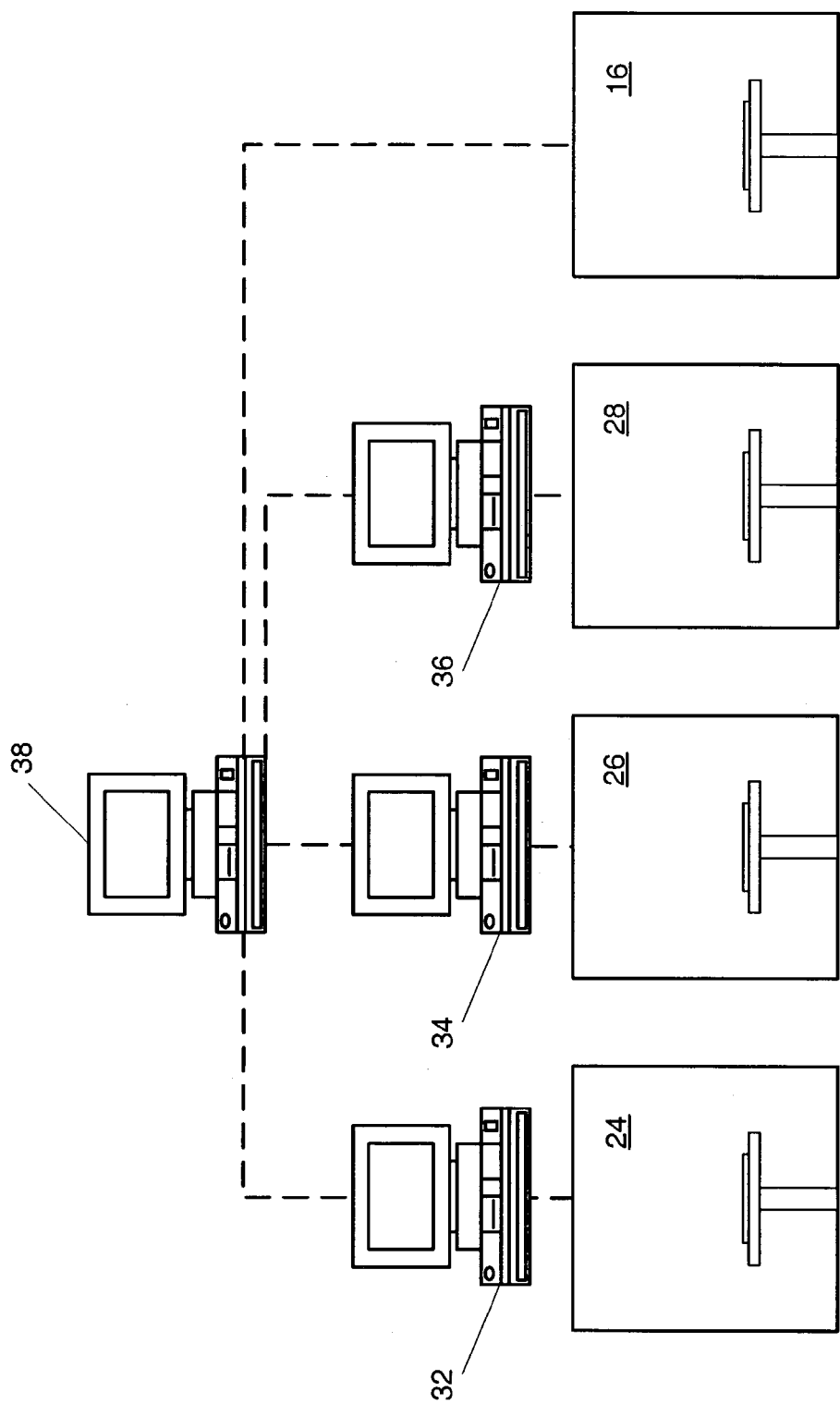

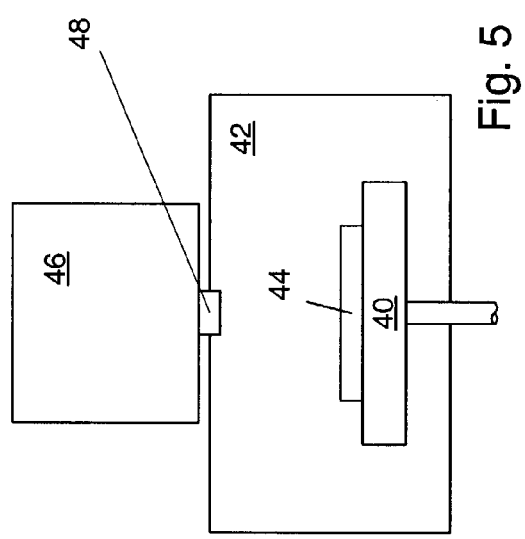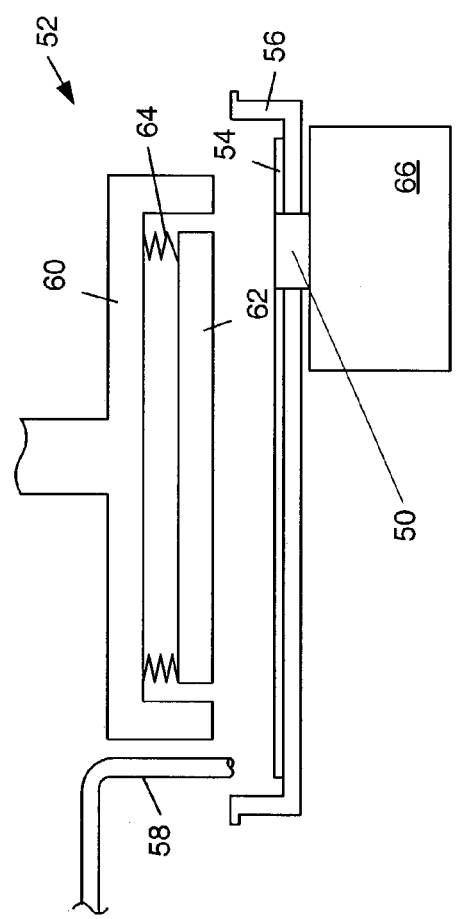

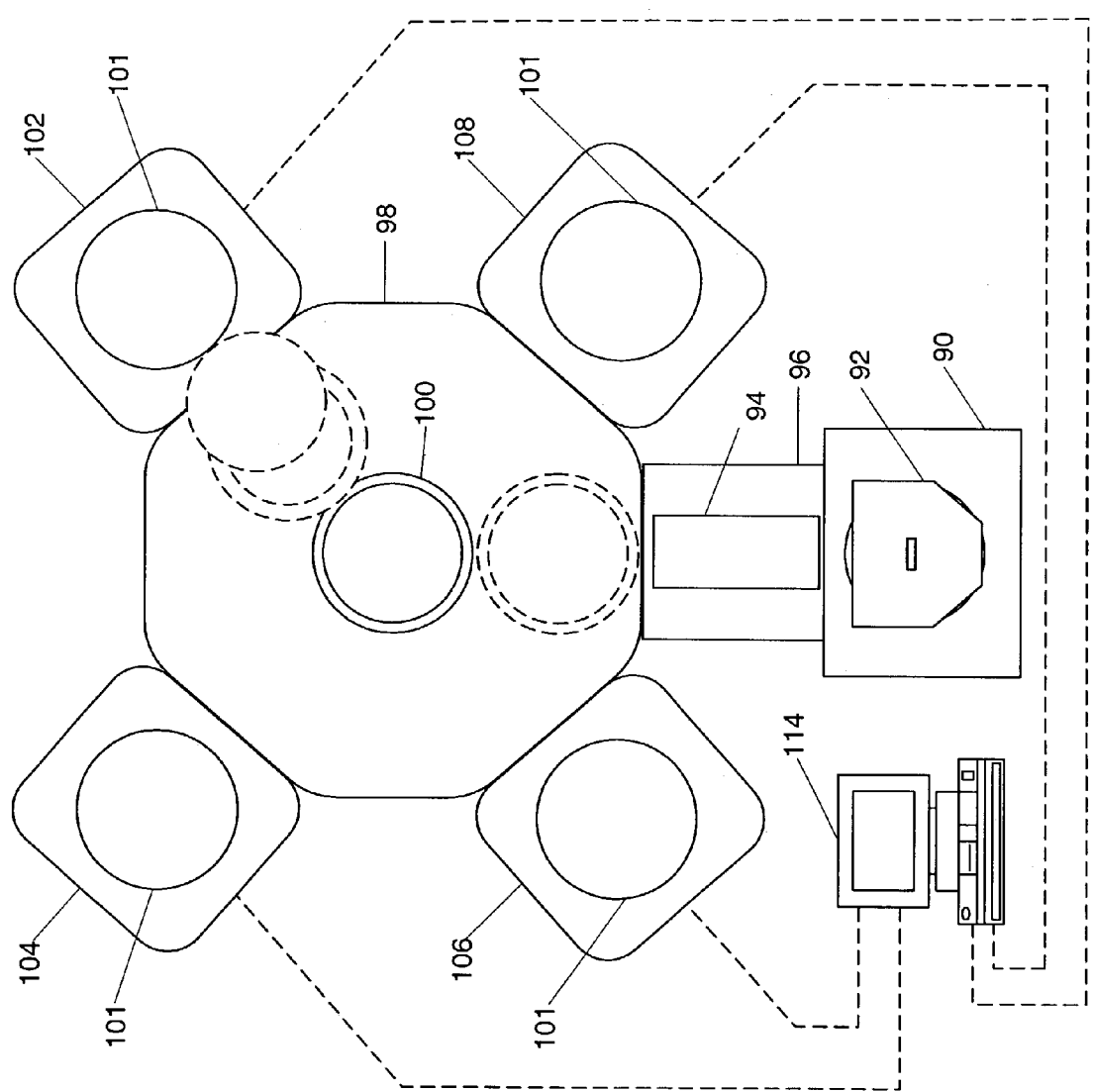

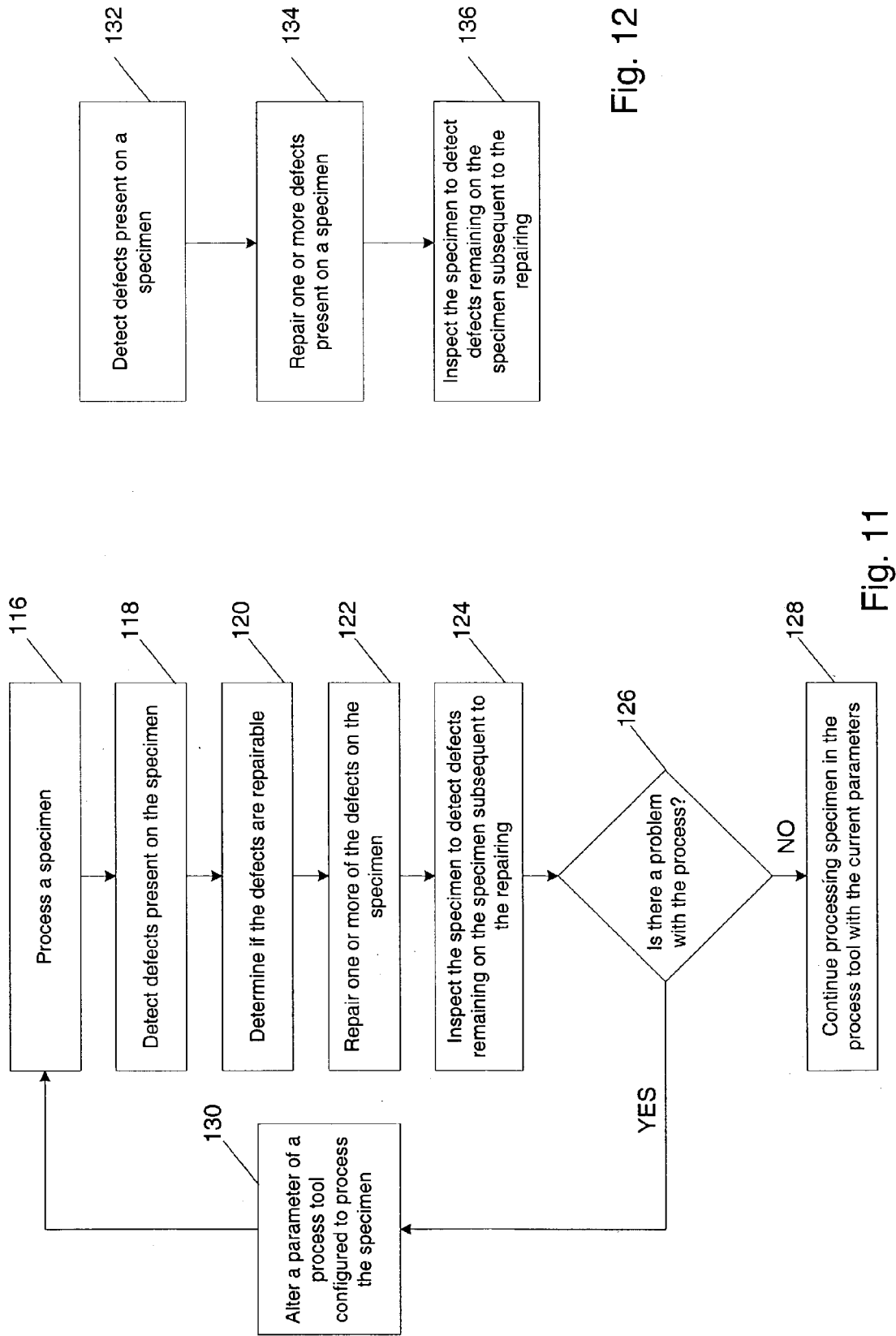

SYSTEMS AND METHODS FOR CLOSED LOOP DEFECT REDUCTION

PRIORITY CLAIM

This application claims priority to U.S. Provisional Application No. 60/349,323 entitled "Systems and Methods for Closed Loop Defect Reduction," filed Jan. 16, 2002.

BACKGROUND OF THE INVENTION

1. Field of the Invention

The present invention generally relates to systems and methods for closed loop defect repair and reduction of defects on subsequent wafers. Certain embodiments relate to systems and methods for detecting defects on a specimen, repairing the detected defects on the specimen, and reducing defects on a subsequent specimen.

2. Description of the Related Art

Fabricating semiconductor devices such as logic and memory devices may typically include processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes may include, but are not limited to, chemical-mechanical polishing, etch, deposition, and ion implantation. Multiple semiconductor devices may be fabricated in an arrangement on a semiconductor wafer and then separated into individual semiconductor devices.

During each semiconductor fabrication process, defects such as particulate contamination and pattern defects may be introduced into semiconductor devices. Such defects may be found either randomly on a specimen surface or may be repeated within each device formed on a specimen. For example, random defects may be caused by events such as an unexpected increase in particulate contamination in a manufacturing environment and an unexpected increase in contamination in process chemicals that may be used in fabrication of a semiconductor device. Defects may also be formed in a systematic fashion over time and due to individual process marginalities and interactions of multiple processes. Defects caused by individual process marginalities or by interactions between multiple processes may result in defects such as a film thickness variation or a lateral dimension variation due to dose variation. Such defects may, in turn, result in a defect in a semiconductor device formed on the specimen such as bridging between two conductive structures thereby forming a short between the structures. Defects repeated within each semiconductor device formed on an entire specimen may, for example, be systematically caused by contamination or defects found on a reticle, or a mask. Contamination or defects on a reticle may be transferred along with a device pattern to a resist during a lithography process.

As the dimensions of advanced semiconductor devices continue to shrink, the presence of defects in the semiconductor device limits the successful fabrication, or yield, of a semiconductor device. For example, a reticle defect reproduced in a resist patterned during lithography may cause an open circuit or a short circuit in a semiconductor device formed in subsequent processing. Because fabrication of a semiconductor device includes many complex process steps, the adverse effects of defects on total yield may increase exponentially if an error that is caused by a defect is propagated throughout an entire manufacturing process or operation over time.

SUMMARY OF THE INVENTION

An embodiment of the invention relates to a method for repairing defects on a specimen and reducing the occurrence of defects in subsequent processing. The method may include detecting defects, determining if the defects are repairable, repairing defects, determining if the defects are due to systematic fixable issues with an upstream or downstream process, and providing output to one or more process tools to reduce the occurrence of defects on subsequent specimen. The specimen may include a wafer or a reticle. The method may include processing the specimen, which may include, but is not limited to, forming a layer of material on the specimen, patterning a resist on the specimen, etching the specimen, polishing the specimen, depositing conductive or dielectric thin films, and/or cleaning the specimen. The method may also include detecting defects present on the specimen. The method may further include repairing one or more of the defects on the specimen. The method may include closed loop defect repair. For example, the method may include sending output from a measurement device used for detecting the defects to a repair tool used for repairing the one or more defects. The output may be responsive to the defects present on the specimen. The method may also include processing the output to determine a parameter of an instrument coupled to a process tool used for processing the specimen. Therefore, the method includes processing one or more specimen and providing output to one or more processing tools.

Detecting defects present on the specimen may include determining a characteristic, or signature, of the defects on the specimen or a collection of specimen. For example, the method may include determining if the defects are repairable. The method may include altering a parameter of an instrument coupled to a process tool and/or a repair tool used for repairing the defects in response to the characteristic. In this manner, the method may include repairing defects determined, for example, to repairable. In addition, detecting defects present on the specimen may include determining a location of the defects on the specimen. Such a method may also include altering a parameter of an instrument coupled to a repair tool used for the repairing in response to the location of the defects such that individual defects may be repaired. The method may also include altering a parameter of an instrument coupled to one or more process tools in response to the location of the defects to re-process the specimen, to rework the specimen, or to reduce the occurrence of defects on additional specimen. Detecting defects present on the specimen may also include forming an image of the specimen, multiple specimens, its defects characteristics, individual defect characteristics, and/or a collection of multiple specimens. The method may also include forming a relationship between these images and process tools, process tool parameters or characteristics, and/or measurement tool characteristics or parameters.

Repairing one or more defects on the specimen may be performed subsequent to or during the detecting of defects present on the specimen. Repairing one or more defects on the specimen may include, but is not limited to, removing the one or more defects with chemically assisted laser removal, laser induced shock wave removal, and particle beam assisted repair. In addition, the method may include determining a process tool modification such as, but not limited to, an etch time, etch gas flow rates, etch gas pressure, and polish time.

In an embodiment, the method may include inspecting the specimen to detect defects remaining on the specimen subsequent to the repairing. For example, detecting defects present on the specimen may include determining locations of the defects present on the specimen. Determining locations of defects may be performed in addition to determining, for example, a type of the defects and if the defects are repairable. In this manner, the method may include inspecting the locations of the defects subsequent to the repairing. Alternatively, inspecting the specimen may be performed during repair of the one or more defects. Inspecting the specimen may include forming an image of the specimen, multiple specimens, its defects characteristics, individual defect characteristics, and/or a collection of multiple specimens. The method may also include forming a relationship between these images and process tools, process tool parameters or characteristics, and/or measurement tool characteristics or parameters.

In an embodiment, the method may also include altering a parameter of an instrument coupled to a repair tool used for the repairing in response to the inspecting. The method may further include altering a parameter of an instrument coupled to a process chamber used for the processing in response to the defects remaining on the specimen.

In an embodiment, the method may include determining a characteristic of the specimen or a collection of specimen during the processing with a measurement device used for the detecting. In an additional embodiment, the method may include altering a parameter of an instrument coupled to a process chamber used for the processing in response to the defects detected on the specimen.

A further embodiment relates to an additional method for repairing defects on a specimen and reducing the occurrence of defects on additional specimen. The method may include detecting defects present on the specimen, repairing one or more defects present on the specimen, and inspecting the specimen to detect defects remaining on the specimen subsequent to the repairing. The method may include any additional steps as described herein.

An additional embodiment relates to a system configured to repair defects on a specimen and reducing the occurrence of defects on additional specimen. The system may include a process chamber configured to process the specimen. The process chamber may include, but is not limited to, a deposition chamber, a plating chamber, a thermal growth chamber, a lithography chamber, an etch chamber, a polishing chamber, and a cleaning chamber. The system may also include a measurement device configured to detect defects present on the specimen subsequent to processing by the process chamber. In addition, the system may include a repair tool configured to repair one or more of the defects detected on the specimen. The system may be arranged as a cluster tool. Alternatively, the system may include a plurality of stand alone devices coupled by a network.

The system may further include a processor coupled to the measurement device and the repair tool. The processor may be configured to receive output from the measurement device. The output may be responsive to the defects detected on the specimen. The processor may also be configured to alter a parameter of an instrument coupled to the repair tool in response to the output. For example, the processor may be configured to determine if the detected defects are repairable from the output. In addition, the processor may be configured to alter the parameter of the instrument coupled to the repair tool such that the one or more defects include defects determined to be repairable. Furthermore, the processor may be configured to determine a location of the detected defects on the specimen from the output and to alter a parameter of an instrument coupled to the repair tool in response to the location of the detected defects. In this manner, the repair tool may be configured to repair individual defects present on the specimen. The processor may further be configured to determine a characteristic of the detected defects from the output. Such a processor may also be configured to alter a parameter of an instrument coupled to the process tool in response to the characteristic of the detected defects. In this manner, the system may be configured to repair defects and to reduce the occurrence of defects on additional specimen.

The measurement device may be configured to form an image of a specimen, multiple specimens, its defects characteristics, individual defect characteristics, and/or a collection of multiple specimens. A processor of the system may be configured to determine a relationship between these images and process tools, process tool parameters or characteristics, and/or measurement tool characteristics or parameters. The measurement device may also be configured to generate additional output during the process. The processor may be configured to obtain a signature characterizing the process from the additional output. In addition, the processor may be configured to alter a parameter of an instrument coupled to the process chamber in response to the signature. The measurement device may also be configured to inspect the specimen to detect defects remaining on the specimen subsequent to repair.

The repair tool may be configured to repair the one or more defects detected on the specimen during detection of the defects by the measurement device. The repair tool may include, but is not limited to, a chemically assisted laser removal tool, a laser induced shock wave removal tool, a particle beam assisted repair tool, or any other appropriate repair tool known in the art. The repair tool may also be configured as part of the measurement device. For example, the measurement device and the repair tool may share a common power source, a common stage, a common handler, and/or a common processor.

In an embodiment, the system may include an inspection tool configured to inspect the specimen to detect defects remaining on the specimen subsequent to repair. The inspection tool may be coupled to the processor. The inspection tool may be configured to receive output from the processor responsive to locations of the detected defects on the specimen. The inspection tool may be configured to inspect the locations on the specimen subsequent to repair to detect defects remaining on the specimen subsequent to repair. The inspection tool may also be configured to form an image of a specimen, multiple specimens, its defects characteristics, individual defect characteristics, and/or a collection of multiple specimens. A processor of the system may be configured to determine a relationship between these images and process tools, process tool parameters or characteristics, and/or measurement tool characteristics or parameters.

In an embodiment, the processor may be coupled to the inspection tool such that the processor may receive additional output from the inspection tool. The additional output may be responsive to the defects remaining on the specimen subsequent to repair. The processor may be further configured to alter a parameter of an instrument coupled to the repair tool in response to the additional output.

In an additional embodiment, the processor may be coupled to the process chamber. The processor may be configured to alter a parameter of an instrument coupled to the process chamber in response to the output. The processor may also be coupled to the process chamber and the inspection tool. The processor may be configured to alter a parameter of an instrument coupled to the process chamber in response to the defects remaining on the specimen subsequent to repair.

A further embodiment relates to an additional system configured to repair defects on a specimen and to reduce the occurrence of defects on additional specimen. The system may include a measurement device configured to detect defects present on the specimen. The system may also include a repair tool configured to repair one or more of the defects detected on the specimen. The system may further include an inspection tool configured to detect defects remaining on the specimen subsequent to repair. In addition, the system may include a processor coupled to the measurement device and the repair tool. The processor may be configured to receive output from the measurement device. The output may be responsive to the defects detected on the specimen. The processor may also be configured to alter a parameter of an instrument coupled to the repair tool in response to the output. The system may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIGS. 3 and 4 depict schematic network diagrams of various embodiments of a system configured to repair defects on a specimen;

FIGS. 5–7 depict schematic cross-sectional views of various embodiments of a measurement device coupled to a process chamber;

FIG. 9 depicts a schematic top view of an embodiment of a system configured to repair defects on a specimen;

FIGS. 11 and 12 depict flow charts illustrating various embodiments of a method for repairing defects on a specimen.

Figure 1:
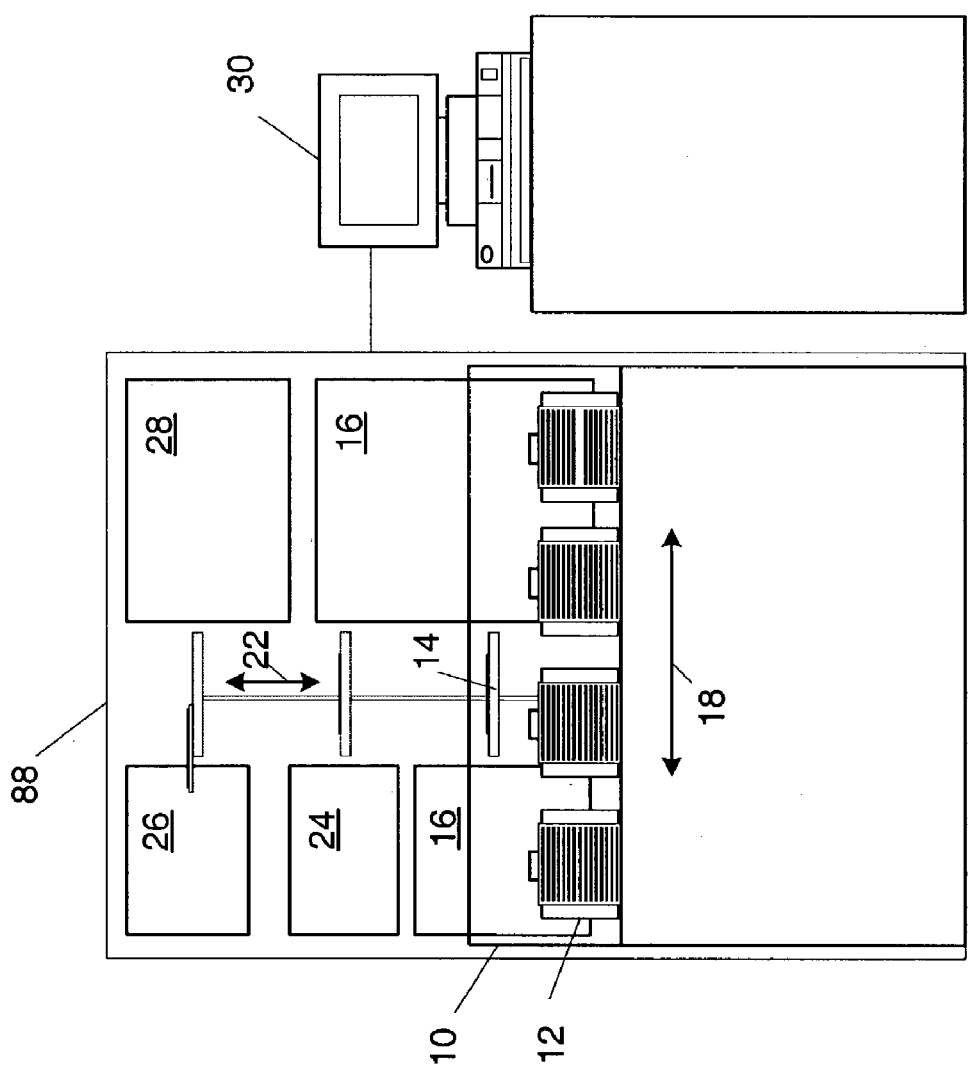
FIG. 1 depicts a schematic side view of an embodiment of a system configured to repair defects on a specimen.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The following description generally relates to systems and methods for repairing defects on a specimen. As used herein, the term "defect" generally refers to an abnormality formed on or within a specimen that may adversely affect the performance or functionality of a device formed on the specimen (i.e., reduce a characteristic such as speed or cause a device failure that may or may not cause a device to be non-working) or additional devices formed on the specimen if the cause is not fixed. Defects may be caused by individual process marginalities. Defects may also be caused by process integration marginalities or interactions between multiple processes. For example, a defect may be contamination on a specimen, abnormal structures on the specimen, or damage to the specimen. Contamination may include, but is not limited to, particles, fibers, or residual material remaining on a specimen after a process step. Contamination may also include organic or inorganic material such as resist, a dielectric material, and/or a conductive material. Abnormal structures on a specimen may include, but are not limited to, missing structures, bridging structures, voids formed within structures, structures that have a lateral dimension that is larger or smaller than a predetermined range of values, and/or structures having an abnormal profile such as roughness, fluting, rounding, and/or a sidewall angle that is larger or smaller than a predetermined range of values. Damage to the specimen may include, for example, a surface scratch, roughness, breakage or the specimen, or breakage of structures formed on the specimen. As used herein, "structures" generally refers to an unpatterned layer of material formed on a specimen, patterned features formed on a specimen, or any combination thereof.

A defect may be present in any location on a specimen. In addition, any number of each of the defects may also be present on the specimen. Furthermore, any number of each of the defects may also be present on any surface of the specimen such as a frontside and/or backside surfaces of a specimen. A defect may also be microscopic in nature (i.e., not visible to the human eye) or macroscopic in nature (i.e., visible to the human eye).

As used herein, "repairing defects" is generally defined as processing a specimen, which may include altering material on the specimen (i.e., removing and/or adding material to the specimen), to remove contamination from the specimen, to alter an abnormal structure of a specimen, and/or to at least partially correct damage to a specimen.

As used herein, a "specimen" is generally defined to include a wafer or a reticle. A collection of specimen may include, but is not limited to, two or more specimen of a lot or a batch. The term "wafer" generally refers to substrates formed of a semiconductor or a non-semiconductor material. Examples of such a semiconductor or a non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer or a wafer prior to a first-pass lithography process. Alternatively, a wafer may include one or more layers that may be formed upon a semiconductor substrate. For example, such layers may include, but are not limited to, a resist, a dielectric material, and a conductive material. A resist may include a resist that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., CORAL™ commercially available from Novellus Systems, Inc., San Jose, Calif., "ultra-low k" dielectric materials such as "zero gels," and "high-k" dielectric materials such as tantalum pentoxide. In addition, examples of a conductive material may include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

A "reticle," or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source.

Figure 2:
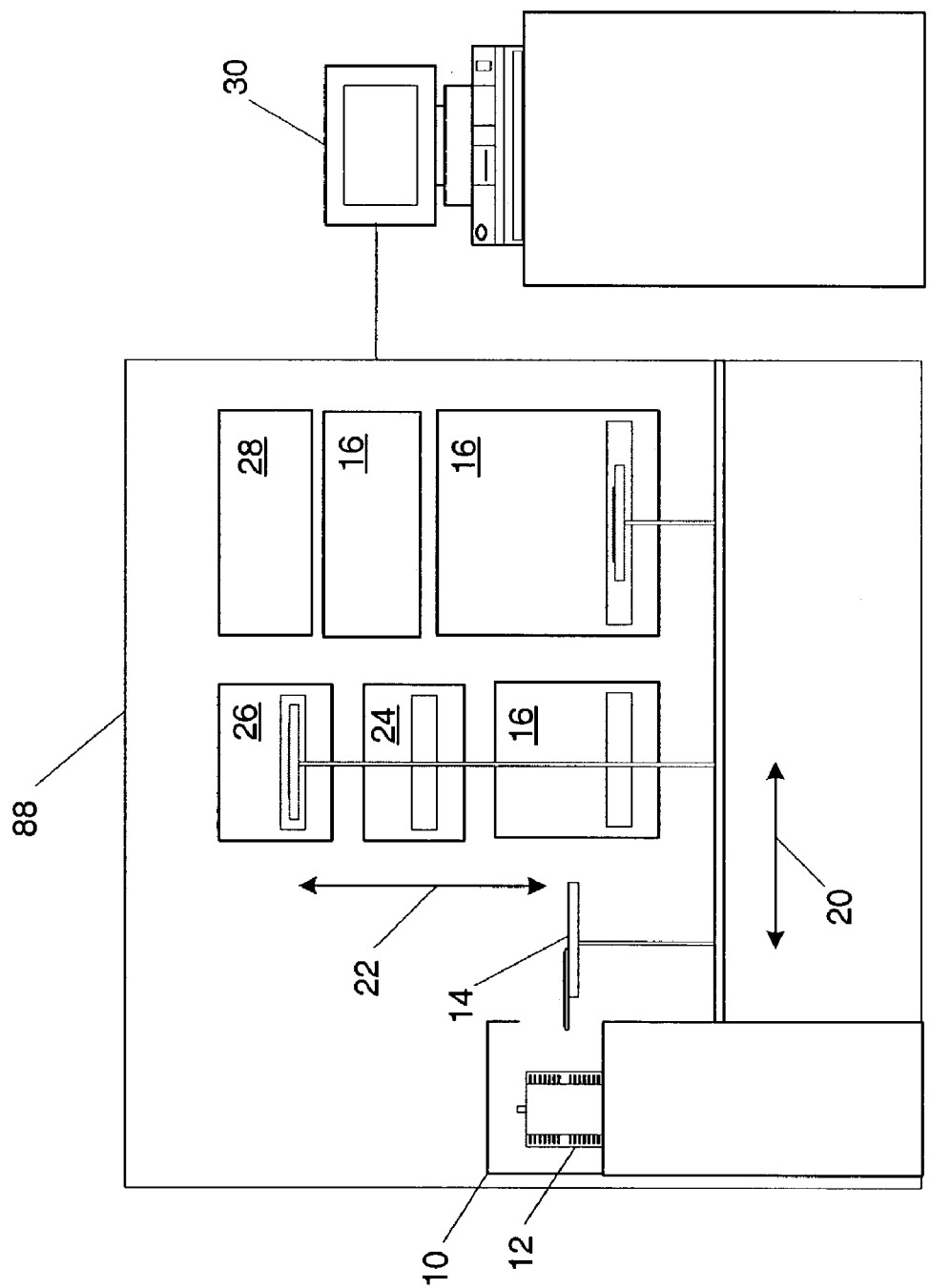
FIG. 2 depicts a schematic cross-sectional view of an embodiment of a system configured to repair defects on a specimen.

Turning now to the drawings, FIG. 1 illustrates a side view of an embodiment of a system configured to repair defects on a specimen. FIG. 2 illustrates a cross-sectional view of the system. As such, elements which are shown in both FIGS. 1 and 2 have been indicated using the same reference numerals. The system may include load chamber 10. Load chamber 10 may be configured to support a number of cassettes 12. The cassettes may be configured to hold a number of specimens to be processed by the process chamber. For example, the cassettes may be front opening unified pods ("FOUP") or any other cassettes known in the art. In addition, load chamber 10 may be configured in a Standard Mechanical Interface ("SMIF") technique such that the load chamber may automatically receive cassettes from another system.

The system may also include at least one robotic specimen handler 14. Robotic wafer handler 14 may be configured to move a specimen from cassette 12 to process chamber 16. For example, the robotic wafer handler may be configured to move laterally along direction 18 in front of cassettes 12. The robotic wafer handler may also be configured to remove a specimen from a cassette and to move the specimen out of load chamber 10. For example, the robotic wafer handler may be configured to move in lateral direction 20, as shown in FIG. 2 in phantom, out of load chamber 10 to process chamber 16. The robotic wafer handler may also be configured to move in vertical direction 22, as shown in FIGS. 1 and 2 in phantom. In this manner, the robotic wafer handler may be configured to laterally and/or vertically move a specimen to a process chamber in the system. In addition, robotic wafer handler 14 may be configured to move a specimen from a first process chamber to a second process chamber. For example, the robotic wafer handler may also be configured to rotate such that a specimen may be moved from a first process chamber located on a first side of the system to a second process chamber located on a second side of the system. The first side and the second side may be located on substantially opposite sides of the lithography tool. In this manner, the robotic wafer handler may move a specimen sequentially through a series of process chambers such that a process may be performed on the specimen. In a similar manner, the robotic wafer handler may also move a specimen from a process chamber to a measurement device, from a measurement device to a repair tool, from a measurement device to a process chamber, from a repair tool to an inspection tool and/or from an inspection tool to a process chamber.

The system may also include process chamber 16 configured to process a specimen. For example, process chamber 16 may include a deposition chamber, a plating chamber, a thermal growth chamber, a lithography chamber, an etch chamber, a polishing chamber, or a cleaning chamber. Examples of a deposition chamber may include a chemical vapor deposition chamber, a physical vapor deposition chamber, an atomic layer deposition chamber, or any other deposition chamber known in the art. Such deposition chambers are commercially available, for example, from Applied Materials, Inc., Santa Clara, Calif. A plating chamber may be configured to form a layer of metal upon a specimen such as a wafer. A thermal growth chamber may be configured to grow a layer silicon dioxide on a specimen by heating the specimen to a temperature of greater than about 700° C. in an oxidizing ambient such as $O_2$ or $H_2O$. Such plating and thermal growth chambers are known in the art and are commercially available. A lithography chamber may include, for example, a resist apply chamber, a post apply bake chamber, an exposure chamber, a post exposure bake chamber, or a develop chamber. Such chambers are commercially available, for example, from Tokyo Electron Limited, Minato-ku, Tokyo, Japan. A polishing chamber may be, for example, a chemical mechanical polishing ("CMP") tool. An etch chamber may be a plasma etch chamber, a reactive ion etch ("RIE") chamber, or any other etch chamber known in the art. Such polishing and etch chambers are commercially available from Applied Materials, Inc., Santa Clara, Calif. Examples of a cleaning chamber may include a wet cleaning chamber or a dry cleaning chamber. Such chambers are commercially available from Novellus Systems, Inc., (Gasonics International Corporation), San Jose, Calif. and FSI International, Inc., Chaska, Minn. Process chamber 16, however, may also include any other process chamber known in the art such as an epitaxial deposition chamber commercially available from Applied Materials, Inc., Santa Clara, Calif.

The system may further include a plurality of process chambers 16. For example, the process chambers may be arranged laterally and vertically proximate to each other as shown in FIGS. 1 and 2. Each of the process chambers may be similarly configured or may be configured differently. For example, each of the plurality of process chambers may be configured to form a layer of material on a specimen, for example, by deposition. Alternatively, each of the process chambers may be configured to perform a different step of a process such as a lithography process. In this manner, in combination, the plurality of process chambers may be configured to pattern a resist.

In an embodiment, the system may also include measurement device 24. Measurement device 24 may be configured to detect defects present on the specimen subsequent to processing by process chamber 16. For example, measurement device 24 may be configured to detect defects on the specimen optically or using a charged particle beam such as an electron beam or an ion beam. The measurement device may also be a hybrid measurement device that may use one or more optical methods and/or one or more charged particle beams to detect defects on the specimen. In addition, the measurement device may be configured to form an image of an illuminated portion of the specimen. The measurement system may also be configured to form an image of a specimen, multiple specimens, its defects characteristics, individual defect characteristics, and/or a collection of multiple specimens. A processor of the system may be configured to determine a relationship between these images and process tools, process tool parameters and/or characteristics, and/or measurement tool characteristics and/or parameters.

The measurement device may also include any device known in the art configured to detect defects present on a specimen. For example, the measurement device may be configured to measure a critical dimension of a structure formed on a specimen. Such a measurement device may include, but may not be limited to, a scanning electron microscope or a scatterometer. In addition, the measurement device may be configured to determine an overlay measurement of the specimen. In this manner, the measurement device may include, for example, a Linnik microscope or a scatterometer. The measurement device may also be configured to determine a thickness of a film formed on the specimen. Examples of such a measurement device may include, but are not limited to, an ellipsometer and a reflectometer. Such measurement devices are commercially available from companies including, but not limited to, KLA-Tencor, San Jose, Calif., Applied Materials, Santa Clara, Calif., Hitachi America, Ltd., Schaumburg, Ill., and TSK America, Inc., Bloomfield Hills, Mich.

In addition, the system may include one or more measurement devices. The one or more measurement devices may be configured differently or similarly. In this manner, the system may be configured to detect defects on a number of specimens in parallel. Alternatively, the system may be configured to detect different types of defects on one specimen in series. Examples of systems that include one or more measurement devices are illustrated in U.S. patent application Ser. No. 09/957,468, entitled "Method and systems for determining a critical dimension, a presence of defects and a thin film characteristic of a specimen," by Levy et al., which is incorporated by reference as if fully set forth herein.

Additional examples of methods and measurement devices for determining a presence of defects on a surface of a specimen are illustrated in U.S. Pat. No. 4,247,203 to Levy et al., U.S. Pat. No. 4,347,001 to Levy et al., U.S. Pat. No. 4,378,159 to Galbraith, U.S. Pat. No. 4,448,532 to Joseph et al., U.S. Pat. No. 4,532,650 to Wihl et al., U.S. Pat. No. 4,555,798 to Broadbent, Jr. et al., U.S. Pat. No. 4,556,317 to Sandland et al., U.S. Pat. No. 4,579,455 to Levy et al., U.S. Pat. No. 4,601,576 to Galbraith, U.S. Pat. No. 4,618,938 to Sandland et al., U.S. Pat. No. 4,633,504 to Wihl, U.S. Pat. No. 4,641,967 to Pecen, U.S. Pat. No. 4,644,172 to Sandland et al., U.S. Pat. No. 4,766,324 to Saadat et al., U.S. Pat. No. 4,805,123 to Specht et al., U.S. Pat. No. 4,818,110 to Davidson, U.S. Pat. No. 4,845,558 to Tsai et al., U.S. Pat. No. 4,877,326 to Chadwick et al., U.S. Pat. No. 4,898,471 to Vaught et al., U.S. Pat. No. 4,926,489 to Danielson et al., U.S. Pat. No. 5,076,692 to Neukernans et al., U.S. Pat. No. 5,189,481 to Jann et al., U.S. Pat. No. 5,264,912 to Vaught et al., U.S. Pat. No. 5,355,212 to Wells et al., U.S. Pat. No. 5,537,669 to Evans et al., U.S. Pat. No. 5,563,702 to Emery et al., U.S. Pat. No. 5,565,979 to Gross, U.S. Pat. No. 5,572,598 to Wihl et al., U.S. Pat. No. 5,604,585 to Johnson et al., U.S. Pat. No. 5,737,072 to Emery et al., U.S. Pat. No. 5,798,829 to Vaez-Iravani, U.S. Pat. No. 5,633,747 to Nikoonahad, U.S. Pat. No. 5,822,055 to Tsai et al., U.S. Pat. No. 5,825,482 to Nikoonahad et al., U.S. Pat. No. 5,864,394 to Jordan, III et al., U.S. Pat. No. 5,883,710 to Nikoonahad et al., U.S. Pat. No. 5,917,588 to Addiego, U.S. Pat. No. 6,020,214 to Rosengaus et al., U.S. Pat. No. 6,052,478 to Wihl et al., U.S. Pat. No. 6,064,517 to Chuang et al., U.S. Pat. No. 6,078,386 to Tsai et al., U.S. Pat. No. 6,081,325 to Leslie et al., U.S. Pat. No. 6,175,645 to Elyasaf et al., U.S. Pat. No. 6,178,257 to Alumot et al., U.S. Pat. No. 6,122,046 to Almogy, and U.S. Pat. No. 6,215,551 to Nikoonahad et al., all of which are incorporated by reference as if fully set forth herein. Additional examples of defect inspection methods and measurement devices are illustrated in PCT Application Nos. WO 99/38002 to Elyasaf et al., WO 00/68673 to Reinhron et al., WO 00/70332 to Lehan, WO 01/03145 to Feuerbaum et al., and WO 01/13098 to Almogy et al., and are incorporated by reference as if fully set forth herein. Further examples of defect inspection methods and measurement devices are illustrated in European Patent Application Nos. EP 0 993 019 A2 to Dotan, EP 1 061 358 A2 to Dotan, EP 1 061 571 A2 to Ben-Porath, EP 1 069 609 A2 to Harvey et al., EP 1 081 489 A2 to Karpol et al., EP 1 081 742 A2 to Pearl et al., and EP 1 093 017 A2 to Kenan et al., which are incorporated by reference as if fully set forth herein. As such, the embodiments described herein may also include features of any of the systems and methods illustrated in all of the patents which have been incorporated by reference herein.

The system may also include repair tool 26. Repair tool 26 may be configured to repair one or more individual defects detected on the specimen. The repair tool may be configured to repair one or more defects on the specimen subsequent to detection by the measurement device or during detection by the measurement device. For example, the measurement device may be coupled to the repair tool in a manner similar to coupling of a measurement device to a process chamber as described herein. The repair tool may also be configured as part of the measurement device. For example, the measurement device and the repair tool may share a common power source, a common stage, a common handler, and/or a common processor. In this manner, both the measurement device and the repair tool may have access to a specimen for measurement and repair while the specimen is disposed on the common stage. The combined measurement device and repair tool may include one or more subsystems for measurement and repair. For example, the combined tool may include an optical subsystem for measurement and an e-beam subsystem for repair, an optical subsystem for measurement and an ion beam subsystem for repair, one or more e-beam subsystems for measurement and repair, and any other combination of measurement subsystem and repair subsystem known in the art. In this manner, the system may be combined to switch operation between the various subsystems to perform measurement and repair. In addition, the combined tool may include one or more measurement subsystems and one or more repair subsystems. Furthermore, the various subsystems may be configured to operate substantially simultaneously. In this manner, detection of defects and repair of the detected defects may be performed substantially simultaneously.

The repair tool may be a chemically assisted laser removal tool, a laser induced shock wave removal tool, or a particle beam assisted repair tool. An example of a chemically assisted laser removal tool is illustrated in "Chemically Assisted Laser Removal of Photoresist and Particles from Semiconductor Wafers," by Genut et al. of Oramir Semiconductor Equipment Ltd., Israel, presented at the 28$^{th}$ Annual Meeting of the Fine Particle Society, Apr. 1–3, 1998, which is incorporated by reference as if fully set forth herein. Such a tool may be configured such that gas mixtures used for laser induced combustion and oxidative processes, based on oxygen and nitrogen chemistry, are injected into the stripping process chamber. Excimer laser pulses at 248 nm, at variable repetition rate and variable peak intensities, are incident on the sample utilizing a specially designed optical system. The laser beam is scanned over the entire wafer. During the stripping process, the photoresist and all imbedded contaminants, including inorganic materials, are removed. For example, the removal tool may remove particles from the specimen. The particles may be located on frontside and/or backside surfaces of the specimen. The reaction products are continuously pumped out of the process chamber.

A laser induced shock wave removal tool may be configured such that particles are removed from a surface by using a focused laser beam or other means to produce shock waves at points above the surface proximate to the particles. The particles may be located on the frontside and/or backside surface of the specimen. Each shock wave has a peak pressure gradient sufficient to dislodge and remove any particle on the surface in the vicinity of the shock wave's point of origin. An example of such a removal tool is illustrated in U.S. Pat. No. 5,023,424 to Vaught, which is incorporated by reference as if fully set forth herein.

A particle beam assisted repair tool may be configured to alter material on a specimen, which may include removing material from a specimen or depositing material on a specimen. For example, the repair tool may be configured to drill holes through passivation and to cut metal lines. In addition, the repair tool may be configured to deposit conductive and dielectric materials. A particle beam assisted repair tool may be configured to perform a focused ion beam ("FIB") technique. In this technique, a beam of gallium ions is focused and scanned over the surface of the sample. The interaction of the ion beam with the sample results in ejection of atoms from the surface (sputtering) and the production of secondary electrons and ions. Deposition is also possible in the presence of an organometallic gas under operating conditions configured to decompose the organometallic gas, which adsorbs onto the surface and forms a layer of material. Such a particle beam assisted repair tool is commercially available from, for example, Micrion Corporation, Peabody, Mass.

In an additional embodiment, the system may include inspection tool 28, as shown in FIGS. 1 and 2. Inspection tool 28 may be configured to detect defects remaining on the specimen subsequent to repair. The inspection tool may also be configured to form an image of the specimen. In addition, the inspection tool may be configured to form an image of a specimen, multiple specimens, its defects characteristics, individual defect characteristics, and/or a collection of multiple specimens. A processor of the system may be configured to determine a relationship between these images and process tools, process tool parameters or characteristics, and/or measurement tool characteristics or parameters. The inspection tool may include, for example, a scanning electron microscope ("SEM"). Scanning electron microscopy generally involves scanning an electron beam over a specimen and creating an image of the specimen by detecting electrons that are reflected, scattered, and/or transmitted by the specimen. The image may be a voltage contrast image and may be used to detect or to inspect (i.e., review) defects present of a specimen. Examples of scanning electron microscope systems are illustrated, for example, in U.S. Pat. No. 4,928,010 to Saito et al., U.S. Pat. No. 5,241,176 to Yonezawa, U.S. Pat. No. 5,502,306 to Meisburger et al., U.S. Pat. No. 5,578,821 to Meisburger et al., U.S. Pat. No. 5,665,968 to Meisburger et al., U.S. Pat. No. 5,717,204 to Meisburger et al., U.S. Pat. No. 5,869,833 to Richardson et al., U.S. Pat. No. 5,872,358 to Todokora et al., and U.S. Pat. No. 5,973,323 to Adler et al., and are incorporated by reference as if fully set forth herein. Appropriate scanning electron microscopes are commercially available from KLA-Tencor, San Jose, Calif. The inspection system may be configured to determine if the defects may be electrical defects (i.e., defects that may adversely affect the performance of a device formed on the specimen), and therefore, should be repaired. An example of a method for detecting electrical defects on test structures of a semiconductor die using a voltage contrast image is illustrated in PCT Application No. WO 01/80304 A2 to Satya et al., which is incorporated by reference as if fully set forth herein.

The system may also include a defect review device that may be configured as an inspection tool as described above. For example, the defect review device may be configured to detect defects remaining on the specimen subsequent to repair optically or with a charged particle beam such as an electron beam or an ion beam. The defect review device may also be a hybrid defect review device that may use one or more optical methods and/or one or more charged particle beams to detect defects on the specimen. The defect review device, however, may be configured to have a higher resolution than inspection tool 24. Although detecting defects at a higher resolution may increase the time it takes to inspect a location on the specimen, the defect review device may be configured to inspect fewer locations on the specimen than the inspection tool. For example, the inspection tool may be configured to detect defects on the substantially the entire specimen. Examples of commercially available defect review tools include e-beam tools such as the ev300 available from KLA-Tencor and SEMVISION from Applied Materials, Inc. and optical tools like the CRS from KLA-Tencor and AIMS review station configured to inspect reticles available from Carl Zeiss, Inc.

A processor, which may be configured according to any of the embodiments described herein, may be configured to receive output from the measurement device responsive to locations of the defects detected by the measurement device. The processor may be coupled to the defect review device such that the defect review device may receive output from the processor responsive to the locations of the detected defects. In this manner, the defect review device may be configured to inspect the locations of the detected defects on the specimen subsequent to repair to detect defects remaining on the specimen. As such, the defect review device may be configured to inspect fewer locations than the inspection tool. Therefore, the defect review device may have a higher resolution without having a reduced throughput. Furthermore, in an embodiment, the system may not include a defect review device, and the inspection tool may be configured to detect defects remaining on the specimen subsequent to repair in addition to being configured as described above. For example, the inspection tool may be configured to have variable resolution.

The inspection tool, or defect review device, may be coupled to the measurement device and/or the repair tool in a manner similar to coupling of a measurement device to a process chamber as described herein. The inspection tool, or defect review device, may also be configured as part of the measurement device and/or the repair tool. For example, the inspection tool, or defect review device, and the measurement device and/or the repair tool may share a common power source, a common stage, a common handler, and/or a common processor. As such, both the inspection tool, or defect review device, and the measurement device and/or the repair tool may have access to a specimen for inspection, measurement, and/or repair while the specimen is on the common stage.

In an embodiment, the system may include processor 30, as shown in FIGS. 1 and 2. Processor 30 may be coupled to measurement device 24 and repair tool 26 as shown in the schematic network diagram of FIG. 3. The processor may be configured to receive output from the measurement device. The output may be responsive to the defects detected on the specimen by the measurement device. The processor may be further configured to alter a parameter of an instrument coupled to the repair tool in response to the output. For example, processor 30 may be configured to determine if the detected defects are repairable from the output from the measurement device. In addition, the processor may be configured to alter a parameter of an instrument coupled to the repair tool such that the repair tool repairs only those defects determined to be repairable.

The processor may also be configured to determine if the specimen should be reworked based on the number of defects on the specimen, the type of defects on the specimen, or another characteristic of the defects on the specimen. Alternatively, the processor may provide such information to an operator, or a process engineer, such that the operator may determine if reworking the specimen may be performed. An example of a rework process may include stripping a resist from a specimen subsequent to a lithography step due to the number of defects on the wafer and repeating the lithography step on the specimen. In some processes, reworking of the specimen may not be possible. Furthermore, the processor may be configured to determine if a specimen should be further processed instead of repaired due to the number, type, or another characteristic of defects on the specimen. For example, a process tool may be used to clean a specimen. A measurement device may be used to detect defects on the specimen subsequent to the cleaning. If the number of defects is above a predetermined number, then, the specimen may be re-cleaned instead of repairing individual defects. The measurement device may be used to re-detect the number of defects on the specimen subsequent to re-cleaning.

In addition, the processor may be configured to determine if the defects that are detected are in critical or non-critical portions of the specimen. For example, the processor may be configured to determine if a defect is in a critical or non-critical portion of the specimen using information provided to the processor from a database such as a reticle database, a floorplan, or a netlist. In this manner, the processor may determine, which defects are to be repaired. For example, the processor may determine that only defects in critical portions of the specimen are to be repaired. In this manner, the processor may alter a parameter of an instrument coupled to the repair tool such that defects in the critical portion, but not the non-critical portion, of the specimen are repaired. Examples of a method for determining if a defect is in a critical portion of a specimen are illustrated in U.S. patent application Ser. No. 10/139,109 entitled "Capturing Designer Intent in Reticle Inspection" filed May 2, 2002 and PCT Application No. WO 00/36525 by Glasser et al., which are incorporated by reference as if fully set forth herein.

The processor may also be configured to determine a location and/or a characteristic of the detected defects on the specimen from output from the measurement device. Furthermore, the processor may be configured to alter a parameter of an instrument coupled to the repair tool in response to the location and/or the characteristic of the detected defects. For example, the processor may essentially convert coordinates of the measurement device into coordinates of the repair tool. Alternatively, if the measurement device and the repair tool share a common stage, the coordinates of the measurement device and the repair tool may be substantially the same thereby eliminating converting coordinates of one tool into another. In addition, the processor may provide information from the measurement device to the repair tool related to defect characteristics such as size and type. In a similar manner, the processor may convert coordinates of the measurement device into coordinates of the inspection tool. As such, the processor may be configured to alter a parameter of an instrument coupled to the inspection tool such that the inspection tool only inspects those defects which were repaired. In addition, the measurement device and the inspection tool may also share a common stage. In this manner, the coordinates of the measurement device and the inspection tool may be substantially the same.

The processor may be further configured to generate output in response to the detected defects. The output may include a visual signal, an audible signal, a collection of information generated from the measurement device such as, but not limited to, locations of defects, characteristics of defects, and if the defects are repairable. In addition, the output may include any output that may provide information about the specimen, defects on the specimen, the process tool, the measurement tool, and the repair tool to an operator, or a process engineer.

As such, the processor may be configured to control the repair tool using a feedforward control technique. In this manner, the system may be configured to perform closed loop defect removal and/or repair. Such closed loop defect removal and/or repair may improve efficiency and thoroughness of yield management processes. For example, defects may be randomly (i.e., non-linearly) formed on a specimen; therefore, identifying and controlling causes of defect formation may be highly unpredictable. As such, conventional control methods may not sufficiently reduce defect formation on a specimen. Therefore, a method as described herein, which may be used to remove or repair defects as they are formed on a specimen in combination with or instead of conventional yield management processes, may be substantially more effective to reduce defects on a specimen than conventional yield management processes alone. In addition, the system may be configured such that repair is performed on a specimen only at locations at which defects are determined to be present. In contrast, conventional cleaning of a specimen may be performed on an entire specimen without correction of specific defects regardless of the defects present on the specimen.

Figure 3:
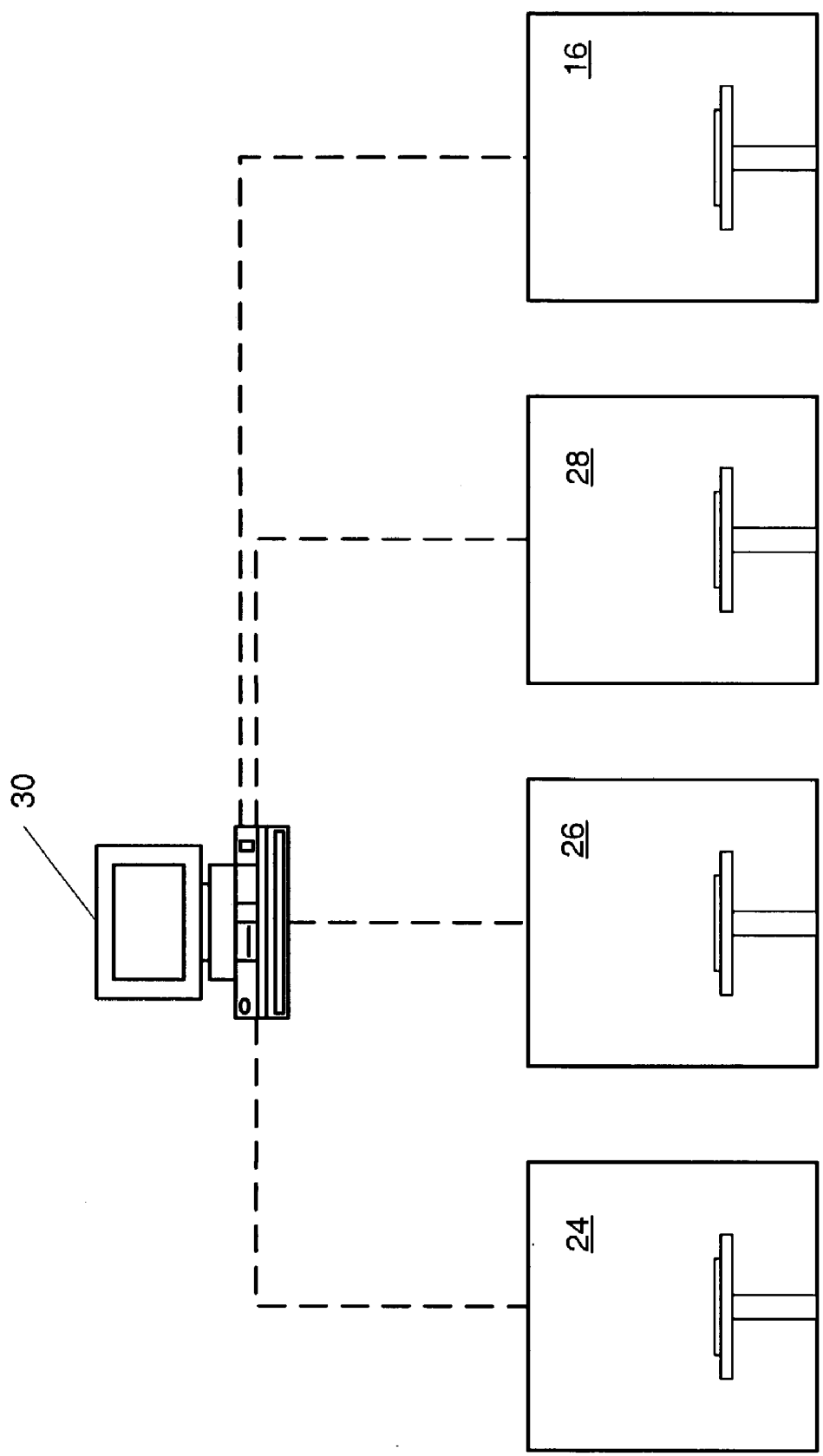

Processor 30 may also be configured to control the repair tool using a feedback control technique and/or an in situ control technique. For example, processor 30 may be coupled to inspection tool 28, as shown in FIG. 3. The processor may be configured to receive output from the inspection tool responsive to the defects remaining on the specimen subsequent to repair using the repair tool. In addition, the processor may be configured to alter a parameter of an instrument coupled to the repair tool in response to the output from the inspection tool. For example, the processor may be configured to control the repair tool during additional repair of the specimen subsequent to inspection. As such, specific defects, which may remain after repair, may be removed in an additional repair step. The processor may also be configured to control the measurement device using a feedback control technique, a feedforward control technique, and/or an in situ control technique.

Processor 30 may also be coupled to process chamber 16, as shown in FIG. 3. The processor may be configured to alter a parameter of the process chamber. For example, the processor may be configured to alter a parameter of an instrument coupled to the process chamber in response to output from the inspection tool, which may indicate the defects remaining on the specimen subsequent to repair. As such, the processor may control the process chamber using a feedback control technique such that fewer unrepairable defects may be formed on the specimen during processing in the process chamber. In addition, the processor may control the process chamber using a feedforward control technique for further processing of the specimen that was inspected. For example, under-etched vias may be detected from a voltage contrast image produced with an inspection tool such as a SEM, and the processor may control the process chamber to increase the etch time of subsequent specimen and/or to set the conditions for further etching of the same specimen to further open the under-etched vias. For example, the processor may also be configured to determine if the defects may be electrical defects and/or may adversely affect the performance of the device, and therefore, need to be repaired. The processor may use a voltage contrast image to determine if the defects on the detected on the specimen may be electrical defects and/or may adversely affect the performance of a device formed on the specimen (i.e., cause an electrical failure such as a short or an open, reduce the speed of a device formed on a specimen, render the device non-working). An example of a method for detecting electrical defects on test structures of a semiconductor die is illustrated in PCT Application No. WO 01/80304 A2 to Satya et al., which is incorporated by reference as if fully set forth herein.

In a similar manner, the processor may be configured to alter a parameter of an instrument coupled to the process chamber in response to output from the measurement device. Therefore, the processor may control the process chamber using a feedback control technique or a feedforward control technique such that fewer total defects (e.g., repairable and/or unrepairable) may be formed on the specimen during processing in the process chamber. Using a feedforward control technique for further processing of a specimen on which defects have been detected by the measurement device, the process chamber may function as a repair tool as described herein.

The system may, therefore, be configured to perform closed loop defect reduction in addition to closed loop defect repair described herein. Such closed loop defect reduction may improve the efficiency and thoroughness of yield management processes. In addition, such closed loop defect reduction may increase the yield of semiconductor manufacturing processes. As described above, for example, defects may be randomly (i.e., non-linearly) formed on a specimen. As such, identifying and controlling causes of defect formation may be highly unpredictable. For example, conventional advanced process control methods may not sufficiently reduce defect formation on specimen because such control methods are designed to reduce defects that may be systematically (i.e., linearly) formed on a specimen. In this manner, a method as described herein, which may be used for closed loop defect reduction in combination with or instead of conventional yield management process, may reduce substantially more defects on specimen than conventional yield management processes alone.

The processor may use feedforward or feedback algorithms to alter a parameter of an instrument coupled to a process tool. The feedforward or feedback algorithms may include algorithms that include variables for, but not limited to, the specific process tool that processed the specimen, the process parameter used to process specimen, a history of the process tools and/or process steps performed on the specimen, and the maintenance history of the process tool. The algorithms may run in conjunction with advanced process control algorithms that may be included in commercially available software such as Catalyst available from KLA-Tencor. Data for the above variables may include information collected from process tools throughout a fab and may be organized and stored in a fab database.

As illustrated in FIG. 3, the system may include a single processor coupled to one or more elements of the system, namely, a process chamber, a measurement device, a repair tool, and an inspection tool. FIG. 4 illustrates a schematic network diagram of an additional embodiment of the system that includes multiple processors. The system may include local processors coupled to one or more elements of the system. For example, the system may include processor 32 coupled to measurement device 24, processor 34 coupled to repair tool 26, and processor 36 coupled to inspection tool 28. One or more of the local processors may be coupled to a remote processor. For example, local processors 32, 34, and 36 may be coupled to remote processor 38, as shown in FIG. 4. In this manner, remote processor 38 may be indirectly coupled to measurement device 24, repair tool 26, and inspection tool 28. Remote processor 38 may also be coupled directly to one or more elements of the system. For example, as shown in phantom in FIG. 4, remote processor 38 may be directly coupled to process chamber 16. An appropriate configuration for the processor or processors included in the system, however, may vary depending upon, for example, the performance capability of each of the processors, the operations to be performed by each of the processors, and an acceptable run time for each of the operations.

In an additional embodiment, the measurement device may be configured to detect defects on a specimen during processing of the specimen in the process chamber. For example, the measurement device may be coupled to the process chamber, as shown in FIGS. 5 and 6. As shown in FIG. 5, stage 40 may be disposed within process chamber 42. The process chamber may include, for example, a deposition process chamber, a thermal growth process chamber, a lithography process chamber, or an etch process chamber as described herein. Stage 40 may be configured to support specimen 44, for example, during processing of the specimen in the process chamber. Measurement device 46 may be coupled to process chamber 42 such that the measurement device may be external to process chamber 42 but may be coupled to stage 40 disposed within the process chamber. For example, process chamber 42 may include one or more relatively small sections 48 of a substantially transparent material disposed within one or more walls of the process chamber. Sections 48 may be configured to transmit a beam of energy from an energy source of the measurement device outside the process chamber to a surface of a specimen within the process chamber. Sections 48 may also be configured to transmit a beam of energy returned from the surface of the specimen to a collector or a detector of measurement device 46 outside process chamber 42.

The substantially transparent material may have optical or material properties such that the beam of energy from the energy source and the returned beam of energy may pass through sections 48 of the process chamber without undesirably altering the properties of the directed and returned energy beams. For example, undesirably altering the properties of the energy beams may include, but is not limited to, altering a polarization or a wavelength of the energy beams and increasing chromatic aberration of the energy beams. In addition, sections 48 may be configured such that deposition of process residue from a chemical using during processing of a specimen may be reduced as described in PCT Application No. 99/65056 to Grimbergen et al., which is incorporated by reference as if fully set forth herein. Examples of a measurement device coupled to a process tool are illustrated in U.S. Pat. No. 6,020,957 to Rosengaus et al. and U.S. patent application Ser. No. 09/956,849 entitled "Methods and systems for determining a property of a specimen prior to, during, or subsequent to lithography," by Levy et al., which is incorporated by reference as if fully set forth herein.

An appropriate system and method for coupling a measurement device to a process chamber may vary, however, depending on, for example, a configuration of the process chamber and/or a configuration of the measurement device. For example, as shown in FIG. 6, the placement and dimensions of relatively small section 50 disposed within the walls of process chamber 52 may vary depending upon the process chamber. FIG. 6 illustrates a portion of a chemical mechanical polishing tool in which relatively small section 50 is disposed within polishing pad 54 and polishing platen 56. Relatively small section 50 may be configured as described above. Polishing platen 56 may be configured to support polishing pad 54. Dispense arm 58 may be configured to dispense a polishing liquid onto polishing pad 54 while polishing head 60 holds specimen 62 against polishing pad 54. Polishing head 60 may include a number of springs 64 or another suitable mechanical device, which may be configured to apply an adjustable pressure to a back side of specimen 62. Polishing head 60 may also be configured to rotate around a central axis of the polishing head. In addition, polishing head 60 may also be configured to move linearly with respect to the polishing platen. In this manner, section 50 may be configured to transmit a beam of energy to and from a specimen during polishing such that measurement device 66 may detect defects on the specimen or another characteristic of the specimen during polishing.

In addition, placement and dimension of the relatively small sections may be altered to reduce, and even substantially eliminate, exposure of a measurement device to chemicals and environmental conditions within a process chamber. Furthermore, a measurement device may be externally coupled to a process chamber such that the measurement device may not alter operation, performance, or control of a process step carried out in the process chamber.

A measurement device, as shown in FIGS. 5 and 6, may be configured to generate output during processing of the specimen in the process chamber. The output of the measurement device may be responsive to defects present on the specimen or to another characteristic of the specimen such as a thickness of a layer formed on the specimen. The measurement device may be configured to generate the output continuously or at various time intervals during processing. In this manner, the processor may be configured to receive the output from the measurement device and to obtain a signature characterizing the process from the output. Furthermore, the processor may be configured to alter a parameter of an instrument coupled to the process chamber in response to the signature. For example, the processor may determine an endpoint of a process from a singularity in the signature. As such, upon determination of the endpoint, the processor may control the process chamber to reduce, and eventually terminate, processing. In addition, the processor may use the signature for in situ control of the process chamber.

Figure 7:
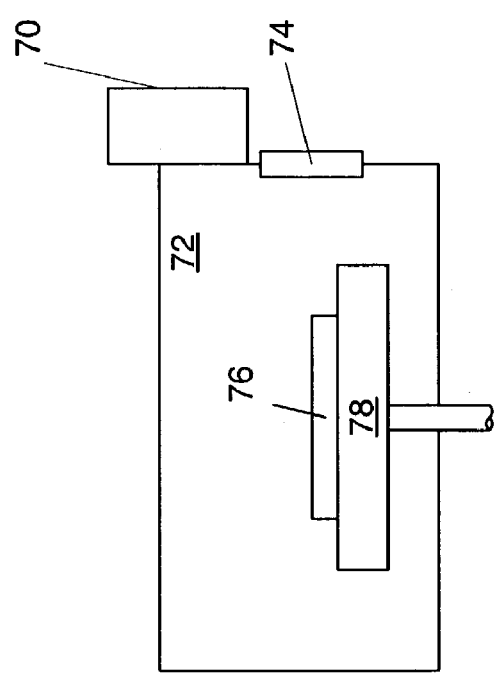

In an additional embodiment, the measurement device may be configured to detect defects or another characteristic of the specimen as the specimen is being transported through the system. For example, FIG. 7 illustrates an embodiment of measurement device 70 coupled to process chamber 72. The process chamber may include chamber opening 74, which may be configured such that specimen 76 may be disposed upon stage 78 within the process chamber by a robotic wafer handler (not shown). As shown in FIG. 7, measurement device 70 may be coupled externally to process chamber 72 such that measurement device 70 may be located proximate chamber opening 74. Although measurement device 70 is shown to be disposed above chamber opening 74 in FIG. 7, measurement device 70 may also be disposed below chamber opening 74. In this manner, measurement device 70 may be configured to detect defects or another characteristic of a specimen on a front side or a back side of the specimen as the specimen is being moved into or out of the process chamber through chamber opening 74 by a wafer robotic handler. The measurement device may also be coupled to a repair tool as shown in FIGS. 5–7.

Figure 8:
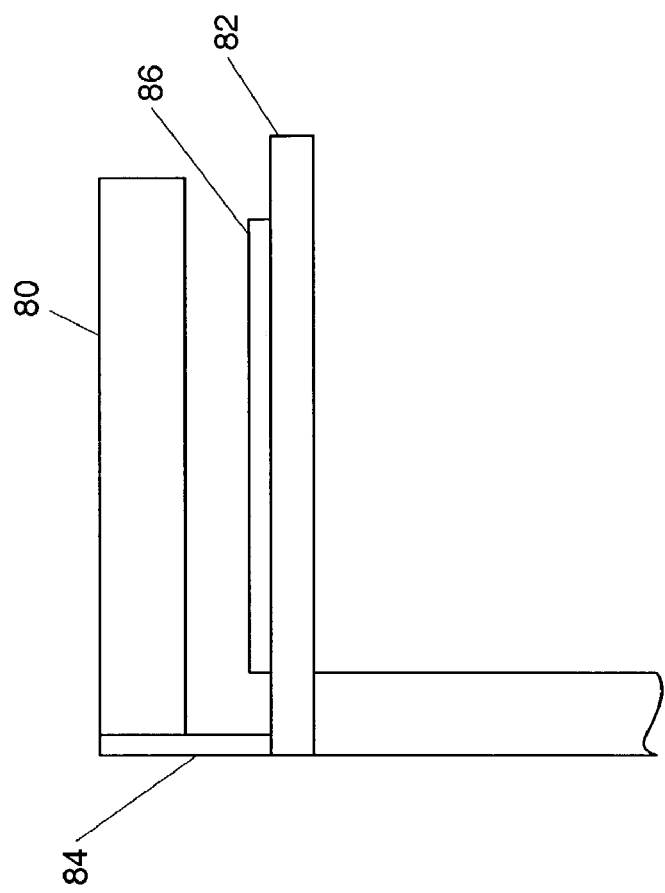
FIG. 8 depicts a schematic side view of an embodiment of a measurement device coupled to a robotic wafer handler.

FIG. 8 illustrates an embodiment of measurement device 80 coupled to robotic wafer handler 82. For example, measurement device 80 may be coupled to the robotic wafer handler by support bar 84. Support bar 84 may be configured to maintain a position of measurement device 80 above handler 82. In addition, support bar 84 may be configured to reduce the effect of vibrations caused by movement of the robotic wafer handler on measurements by the measurement device by absorbing such vibrations. Although measurement device 80 is shown to be disposed above robotic wafer handler 82 in FIG. 8, measurement device 80 may also be disposed below robotic wafer handler 82. In this manner, the measurement device may be configured to detect defects on a front side or a back side of specimen 86 or to determine another characteristic of the specimen as the specimen is being moved within the system. The robotic wafer handler may be configured according to any of the embodiments described herein. Therefore, measurement device 80 may be configured to move with the robotic wafer handler within the system, for example, from the load chamber to a process chamber, from a process chamber to a repair tool, and from the repair tool to an inspection tool or the load chamber. An inspection tool may also be coupled to a process chamber, a repair tool, or a robotic wafer handler as shown in FIGS. 5–8. For example, a SEM inspection tool may be coupled to a FIB repair tool in a common vacuum.

A processor, a local processor, or a remote processor, as described herein, may be a computer system configured to operate software to perform according to the above embodiments. The computer system may include a memory medium on which computer programs may be stored for controlling the system and processing the detected energy. The term "memory medium" is intended to include an installation medium, e.g., a CD-ROM, or floppy disks, a computer system memory such as DRAM, SRAM, EDO RAM, Rambus RAM, etc., or a nonvolatile memory such as a magnetic media, e.g., a hard drive, or optical storage. The memory medium may include other types of memory as well, or combinations thereof. In addition, the memory medium may be located in a first computer in which the programs are executed, or may be located in a second different computer that connects to the first computer over a network. In the latter instance, the second computer provides the program instructions to the first computer for execution. Also, the computer system may take various forms, including a personal computer system, mainframe computer system, workstation, network appliance, Internet appliance, personal digital assistant ("PDA"), television system or other device. In general, the term "computer system" may be broadly defined to encompass any device having a processor, which executes instructions from a memory medium.

The memory medium may be configured to store a software program for the operation of the system to determine at least two properties of a specimen. The software program may be implemented in any of various ways, including procedure-based techniques, component-based techniques, and/or object-oriented techniques, among others. For example, the software program may be implemented using ActiveX controls, C++ objects, JavaBeans, Microsoft Foundation Classes ("MFC"), or other technologies or methodologies, as desired. A CPU, such as the host CPU, executing code and data from the memory medium may include a means for creating and executing the software program according to the methods described above.

Various embodiments further include receiving or storing instructions and/or data implemented in accordance with the foregoing description upon a carrier medium. Suitable carrier media include memory media or storage media such as magnetic or optical media, e.g., disk or CD-ROM, as well as signals such as electrical, electromagnetic, or digital signals, conveyed via a communication medium such as networks and/or a wireless link.

In an embodiment, the system may be arranged as a cluster tool. For example, as shown in FIGS. 1 and 2, load chamber 10, process chamber 16 or a plurality of process chambers, measurement device 24, repair tool 26, and inspection tool 28 may be arranged in unit 88. Environmental conditions within unit 88 may be controlled substantially independently from environmental conditions of the space surrounding the unit. For example, the environment within the unit may be controlled by chemical filtration of atmospheric air or by feeding a supply of sufficiently pure gas. In this manner, the environment within the unit may be controlled such that levels of chemical species including, but not limited to, ammonia and amine-group-containing compounds, water, carbon dioxide, and oxygen may be reduced. In addition, environmental conditions within the unit may be controlled by a processor, which may be coupled to the system and may be configured according to any of the embodiments described herein. For example, environmental conditions within unit 88 such as relative humidity, particulate count, and temperature may be controlled by the processor. Such a unit may be commonly referred to as a "mini-environment." The unit may also include a common handler as described above and a common power source for each element of the system as described above.

Figure 10:
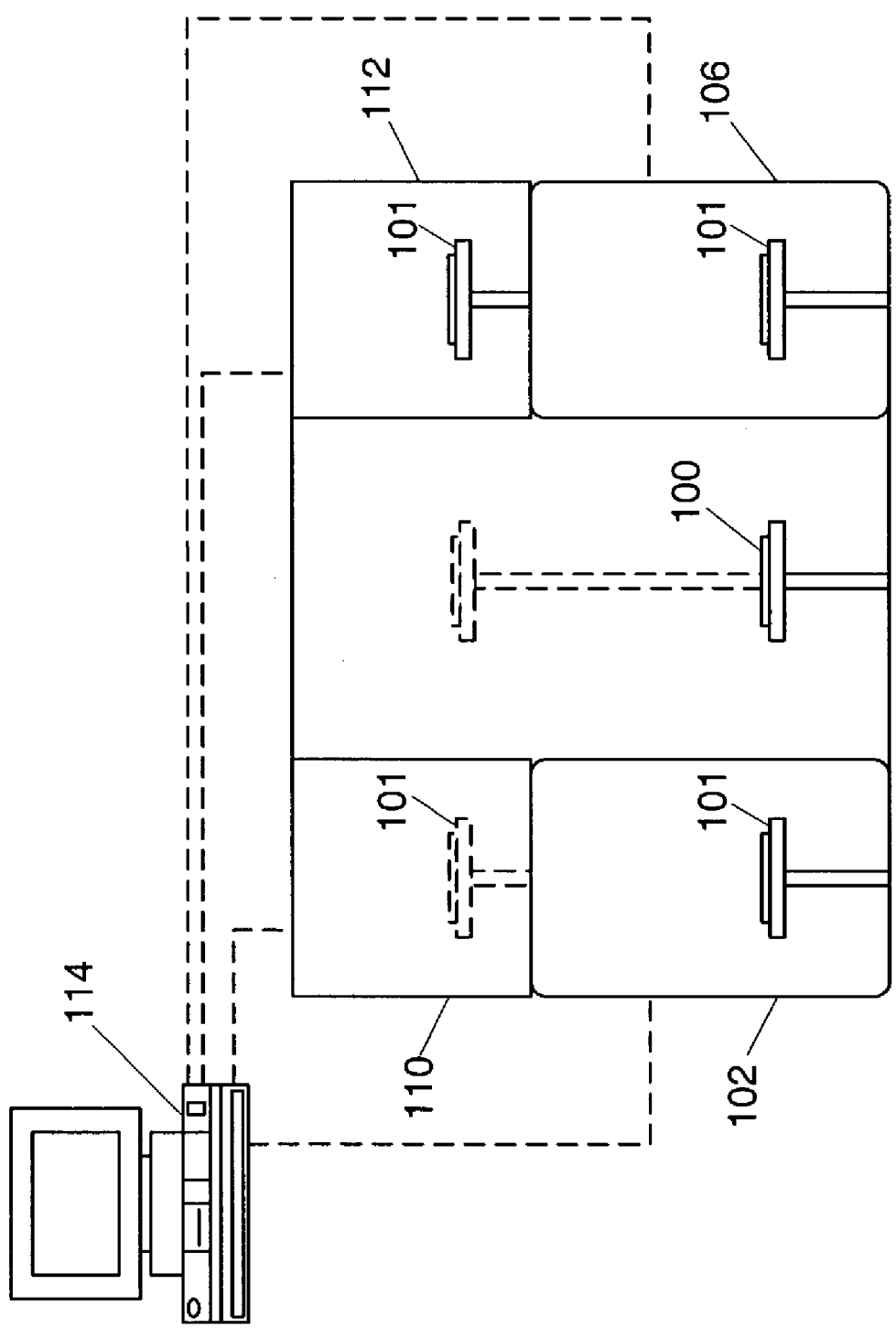
FIG. 10 depicts a schematic cross-sectional view of an embodiment of a system configured to repair defects on a specimen.

FIG. 9 illustrates a top view of an embodiment of a system configured to repair defects on a specimen, which may be configured as a cluster tool. FIG. 10 illustrates a cross-sectional side view of the system. As such, elements, which are shown in both FIGS. 9 and 10, have been indicated using the same reference numerals. As shown in FIG. 9, the system may include load chamber 90, which may be configured as described above. For example, load chamber 90 may be configured to support cassette 92 and/or a number of cassettes. The system may also include wafer transfer chamber 94. Wafer transfer chamber 94 may include wafer transfer arm 96. Wafer transfer arm 96 may be configured to move laterally and vertically to remove a specimen from cassette 92 and to move the specimen into main chamber 98. Main chamber 98 may also include robotic wafer handler 100. Robotic wafer handler 100 may be configured to receive a specimen from wafer transfer arm 96 and to place the specimen upon stage 101 within an additional chamber, device, or tool of the system, as shown in phantom in FIG. 9. Wafer transfer arm 96 and robotic wafer handler 100 may be further configured as described herein. For example, robotic wafer handler 100 may be configured to move vertically as shown in phantom in FIG. 10.

The system may include process chamber 102, measurement device 104, repair tool 106, and/or inspection tool 108, which may be configured as described herein. As shown in FIG. 9, process chamber 102, measurement device 104, repair tool 106, and/or inspection tool 108 may be arranged laterally proximate to each other. In addition, one or more of the elements of the system may be arranged vertically proximate to another of the elements. For example, as shown in FIG. 10, measurement device 110 may be arranged vertically proximate to process chamber 102. In this manner, measurement device 110 may be configured to detect defects present on a specimen during or subsequent to a process carried out in process chamber 102. In addition, inspection tool 112 may be arranged vertically proximate to repair tool 106. In this manner, inspection tool 112 may be configured to inspect a specimen during or subsequent to repair of the specimen in repair tool 106. The system may further include more than one process chamber, more than one measurement device, more than one repair tool, and/or more than one inspection tool. An appropriate arrangement of the process chambers, measurement devices, repair tools, and/or inspection tools may vary depending upon, for example, the number of and operations to be performed by the chambers, devices, and tools included in the system and the footprint available for the system.

In a cluster tool, inspection and/or repair may be performed in a process chamber configured to chill a specimen since the specimen is not otherwise being processed. Scheduling algorithms may be used with the cluster tool and may account for the time needed for processing, detecting defects, and repairing. In a further embodiment, each of the processors as described herein may be configured to automatically generate a schedule for processing, inspection, and repair within a multichamber cluster tool as illustrated in U.S. Pat. No. 6,201,999 to Jevtic and U.S. Pat. No. 6,224,638 to Jevtic, and PCT Application No. WO 98/57358 to Jevtic, which are incorporated by reference as if fully set forth herein.

The processor may also be configured to assign a priority value to process chambers, measurement chambers, and/or repair tools of a cluster tool. The processor may be configured to control a wafer transfer arm and/or a robotic wafer handler of the cluster tool such that a specimen may be moved from chamber to chamber according to the assigned priorities. The processor may also be configured to determine an amount of time available before a priority move is to be performed. If the determined amount of time is sufficient before a priority move is to be performed, the processor may control the wafer transfer arm and/or a robotic wafer handler to perform a non-priority move while waiting. For example, if the determined amount of time is sufficient before a process step is to be performed on a specimen, then the wafer transfer arm and/or a robotic wafer handler may move the specimen to a measurement chamber. In this manner, a system as described herein may be configured to inspect and/or repair the specimen while the specimen is waiting between process steps. The processor may also be configured to dynamically vary assigned priorities depending upon, for example, the availability of process and/or measurement chambers. Furthermore, the processor may assign priorities to the process and/or measurement chambers based upon, for example, a time required for a wafer handler to move the wafer in a particular sequence.

A system as described herein may also include multiple chill process chambers or a multi-slot chill process chamber. Such multiple or multi-slot chill process chambers allows multiple wafers to be cooled while other wafers are subjected to processing steps in other chambers. In addition, each of the processors as described herein may be configured to assign a priority level to each wafer in a processing sequence depending on its processing stage, and this priority level may be used to sequence the movement of wafers between chambers as illustrated in U.S. Pat. No. 6,201,998 to Lin et al., which is incorporated by reference as if fully set forth herein. In this manner, a system as described herein may increase an efficiency at which wafers are transferred among different processing chambers in a wafer processing facility.

The system may also include processor 114, which may be coupled to the process chamber, the measurement device, the repair tool, and/or the inspection tool directly or indirectly as described herein. In addition, processor 114 may be further configured as described herein. The system may also be further configured according to any of the embodiments described herein.

In an alternative embodiment, a system configured to repair defects on a specimen may include a plurality of stand alone systems. For example, the system may include one or more process chambers arranged in a stand alone process tool or in a plurality of stand alone process tools. One or more process chambers may also be arranged in a stand-alone cluster tool, which is coupled to a stand alone cleaning chamber. In such an embodiment, the cluster tool may be coupled to the cleaning chamber by a common handler. The handler may be configured as described above. In one embodiment, the cleaning chamber may be configured to process a single specimen or one specimen at a time. In addition, the system may include one or more measurement devices, which may each be arranged as a stand alone device, or which may be coupled into one stand alone measurement device. The system may also include one or more repair tools arranged in a stand alone repair tool or a plurality of stand alone repair tools. The system may further include one or more inspection tools, which may be arranged as a stand alone inspection tool or a plurality of stand alone inspection tools. The stand alone tools may be physically separate from each other (i.e., nonintegrated) but may use or interpret a common data structure (such as KLARFF, which is commercially available from KLA-Tencor, San Jose, Calif.) to transmit defect information such as location and type from one or more measurement devices or inspection tools to one or more repair tools or to one or more process tools. In some embodiments, the stand alone tools may be physically separate but coupled by a common handler.

FIG. 11 illustrates an embodiment of a method for repairing defects on a specimen and reducing the occurrence of defects on subsequent specimen. The method may include processing a specimen, as shown in step 116. Processing the specimen may include, but is not limited to, forming a layer of material on the specimen, patterning a resist on the specimen, etching the specimen, polishing the specimen, depositing a conductive or dielectric layer on the specimen, and cleaning the specimen. The method may also include detecting defects present on the specimen, as shown in step 118. Detecting defects may be performed as described herein. The method may also include determining if the defects are repairable, as shown in step 120. Detecting defects on the specimen may also include determining a characteristic of the defects on the specimen. In addition, detecting defects on the specimen may include determining a location of the defects on the specimen. Detecting the defects may also include forming an image of the specimen, multiple specimens, its defects characteristics, individual defect characteristics, and/or a collection of multiple specimens. The method may also include forming a relationship between these images and process tools, process tool parameters or characteristics, and/or measurement tool characteristics or parameters.

The method may further include repairing one or more of the defects on the specimen, as shown in step 122. The one or more defects may include defects determined to be repairable. The method may also include altering a parameter of an instrument coupled to a repair tool used for the repairing in response to the characteristic and/or location of the defects. In this manner, the method may include controlling the repair tool using a feedforward control technique. For example, the method may include sending output from a measurement device used for detecting the defects to a repair tool used for repairing the one or more defects. The output may be responsive to the defects present on the specimen. The method may also include processing the output to determine a parameter of an instrument coupled to the repair tool. In addition, the method may include altering the parameter of the instrument such that the parameter of the instrument is approximately the determined parameter prior to or during repair of the one or more defects. In this manner, the method may include closed loop defect repair and/or removal. The repair tool may be configured as described herein. Repairing one or more defects may also be performed during detection of defects on the specimen. Repairing one or more defects may include removing the one or more defects with chemically assisted laser removal, laser induced shock wave removal, and/or particle beam assisted repair.

In an embodiment, the method may also include inspecting the specimen to detect defects remaining on the specimen after repair, as shown in step 124. Inspecting the specimen may be performed as described herein. Inspecting the specimen may be performed subsequent to repair of the specimen or during repair of the specimen. Inspecting the specimen may include inspecting locations on the specimen corresponding to locations at which the measurement device determined a defect to be present. For example, the method may include controlling an inspection tool using a feedforward control technique and output from a measurement device used for the detection of defects on the specimen. Inspecting the specimen may also include forming an image of the specimen, multiple specimens, its defects characteristics, individual defect characteristics, and/or a collection of multiple specimens. The method may also include forming a relationship between these images and process tools, process tool parameters or characteristics, and/or measurement tool characteristics or parameters.

The method may further include altering a parameter of an instrument coupled to a repair tool used for the repairing in response to the inspection of the specimen. For example, the method may include controlling the repair tool using a feedback control technique, a feedforward control technique, and/or an in situ control technique in response to inspection of the specimen. The repair tool may be configured as described herein.

The method may further include altering a parameter of an instrument coupled to a process chamber used for the processing in response to the defects detected on the specimen. For example, the method may include controlling the process chamber using a feedback control technique, a feedforward control technique, and/or an in situ control technique in response to detection of defects on a specimen. In this manner, the method may be used for closed loop defect reduction. Such closed loop defect reduction may be used to reduce defects randomly formed on a specimen as described above. The process chamber may be configured as described herein.

As shown in step 126, the method may include determining if there is a problem with the process used in step 116. For example, the method may include processing data from the measurement device and/or the inspection device to determine if the defects are being formed on the specimen due to individual process marginalities or by interactions of multiple processes. In one embodiment, the defects may be caused by individual process marginalities or by interactions of multiple processes if the defects are also detected on other specimen processed prior to or subsequent to the specimen being repaired. Alternatively, the method may include comparing characteristics, locations, numbers, types and/or any other data about the defects to determine if the characteristics, locations, numbers, types and/or other data are outside of a predetermined range.

If, in step 126, it is determined that there is a problem with the process, then the method may include altering a parameter of a process tool configured to process the specimen, as shown in step 130. If, in step 126, it is not determined that there is a problem with process, then the method may include continuing processing additional specimen in the process tool with the current parameters as shown in step 128. The method may also include any of the additional steps described herein.

The method may also include altering a parameter of an instrument coupled to a process chamber for processing of the specimen in response to the defects remaining on the specimen after repair. For example, the method may include controlling the process chamber using a feedback control technique or a feedforward control technique in response to inspection of the specimen. The process chamber may be configured as described herein. The method may also include determining a characteristic of the specimen during processing of the specimen with a measurement device. The measurement device may be configured as described herein.

FIG. 12 illustrates an alternative embodiment of a method for repairing defects on a specimen. The method may include detecting defects present on a specimen, as shown in step 132. The method may also include repairing one or more defects present on the specimen, as shown in step 134. In addition, the method may include inspecting the specimen to detect defects remaining on the specimen subsequent to the repairing, as shown in step 136. The method may further include any of the steps as described herein.

Further modifications and alternative embodiments of various aspects of the invention may be apparent to those skilled in the art in view of this description. For example, a system that may be configured to repair defects on a specimen and to reduce the occurrence of the defects on additional specimen is provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for repairing defects on a specimen, comprising:
   processing the specimen;
   detecting defects present on the specimen;
   determining if the defects are repairable;
   repairing one or more of the defects on the specimen, wherein the one or more defects comprise defects determined to be repairable;
   inspecting the specimen subsequent to the repairing to detect defects remaining on the specimen; and
   altering a parameter of an instrument coupled to a process chamber used for the processing in response to the defects remaining on the specimen.

2. The method of claim 1, wherein the detecting comprises determining a characteristic of the defects on the specimen, the method further comprising altering a parameter of an instrument coupled to a repair tool used for the repairing in response to the characteristic.

3. The method of claim 1, wherein the detecting comprises determining a location of the defects on the specimen, the method further comprising altering a parameter of an instrument coupled to a repair tool used for the repairing in response to the location of the defects.

4. The method of claim 1, further comprising sending output from a measurement device used for the detecting to a repair tool used for the repairing, wherein the output is responsive to the defects present on the specimen, and processing the output to determine a parameter of an instrument coupled to the repair tool for the repairing.

5. The method of claim 1, wherein the detecting comprises forming an image of the specimen.

6. The method of claim 1, wherein the repairing is performed during the detecting.

7. The method of claim 1, wherein the repairing comprises removing the one or more defects with chemically assisted laser removal.

8. The method of claim 1, wherein the repairing comprises removing the one or more defects with laser induced shock wave removal.

9. The method of claim 1, wherein the repairing comprises particle beam assisted repair.

10. The method of claim 1, further comprising determining a characteristic of the specimen during the processing with a measurement device used for the detecting.

11. The method of claim 1, further comprising altering the parameter of the instrument coupled to the process chamber in response to the defects detected on the specimen.

12. The method of claim 1, wherein the processing is selected from the group consisting of forming a layer of material on the specimen, patterning a resist on the specimen, etching the specimen, polishing the specimen, and cleaning the specimen.

13. A method for repairing defects on a specimen, comprising:
   detecting defects present on the specimen;
   repairing one or more of the defects present on the specimen;

inspecting the specimen to detect defects remaining on the specimen subsequent to the repairing; and altering a parameter of an instrument coupled to a process chamber used for processing the specimen in response to the defects remaining on the specimen.

14. The method of claim 13, wherein the detecting comprises determining locations of the defects present on the specimen, and wherein said inspecting comprises inspecting the locations on the specimen subsequent to the repairing to detect the defects remaining on the specimen.

15. The method of claim 13, wherein the inspecting is performed during the repairing.

16. The method of claim 13, further comprising altering a parameter of an instrument coupled to a repair tool used for the repairing in response to the inspecting.

17. The method of claim 13, wherein the inspecting comprises forming an image of the specimen.

18. A system configured to repair defects on a specimen, comprising:
a process chamber configured to process the specimen;
a measurement device configured to detect defects present on the specimen subsequent to processing by the process chamber;
a repair tool configured to repair one or more of the defects detected on the specimen; and
a processor coupled to the process chamber, the measurement device and the repair tool, wherein the processor is configured to receive output from the measurement device, wherein the output is responsive to the defects detected on the specimen, and wherein the processor is further configured to alter a parameter of an instrument coupled to the repair tool in response to the output and to alter a parameter of an instrument coupled to the process chamber in response to defects remaining on the specimen subsequent to repair.

19. The system of claim 18, wherein the processor is further configured to determine if the detected defects are repairable from the output and to alter the parameter of the instrument coupled to the repair tool such that the one or more defects comprise defects determined to be repairable.

20. The system of claim 18, wherein the processor is further configured to determine a characteristic of the detected defects from the output and to alter the parameter of the instrument coupled to the repair tool in response to the characteristic of the detected defects.

21. The system of claim 18, wherein the processor is further configured to determine a location of the detected defects on the specimen from the output and to alter the parameter of the instrument coupled to the repair tool in response to the location of the detected defects.

22. The system of claim 18, wherein the processor is further configured to alter the parameter of the instrument coupled to the process chamber in response to the output.

23. The system of claim 18, wherein the measurement device is further configured to form an image of the specimen.

24. The system of claim 18, wherein the measurement device is further configured to inspect the specimen to detect the defects remaining on the specimen subsequent to repair.

25. The system of claim 18, further comprising an inspection tool configured to inspect the specimen to detect the defects remaining on the specimen subsequent to repair.

26. The system of claim 18, wherein the repair tool is further configured to repair the one or more defects detected on the specimen during detection of the defects by the measurement device.

27. The system of claim 18, wherein the repair tool comprises a chemically assisted laser removal tool.

28. The system of claim 18, wherein the repair tool comprises a laser induced shock wave removal tool.

29. The system of claim 18, wherein the repair tool comprises a particle beam assisted repair tool.

30. The system of claim 18, wherein the measurement device is further configured to generate additional output during the process, and wherein the processor is further configured to obtain a signature characterizing the process from the additional output.

31. The system of claim 18, wherein the measurement device is further configured to generate additional output during the process, and wherein the processor is further configured to obtain a signature characterizing the process from the additional output and to alter the parameter of the instrument coupled to the process chamber in response to the signature.

32. The system of claim 18, wherein the process chamber is selected from the group consisting of a deposition chamber, a plating chamber, a thermal growth chamber, a lithography chamber, an etch chamber, a polishing chamber, and a cleaning chamber.

33. The system of claim 18, wherein the system is arranged as a cluster tool.

34. A system configured to repair defects on a specimen, comprising:
a measurement device configured to detect defects present on the specimen;
a repair tool configured to repair one or more of the defects detected on the specimen;
an inspection tool configured to detect defects remaining on the specimen subsequent to repair; and
a processor coupled to a process chamber, the measurement device, and the repair tool, wherein the processor is configured to receive output from the measurement device, wherein the output is responsive to the defects detected on the specimen, and wherein the processor is farther configured to alter a parameter of an instrument coupled to the repair tool in response to the output and to alter a parameter of an instrument coupled to the process chamber in response to the defects remaining on the specimen subsequent to repair.

35. The system of claim 34, wherein the processor is further coupled to the inspection tool, wherein the inspection tool is further configured to receive output from the processor responsive to locations of the detected defects on the specimen, and wherein the inspection tool is further configured to inspect the locations on the specimen subsequent to repair to detect the defects remaining on the specimen subsequent to repair.

36. The system of claim 34, wherein the inspection tool is further configured to form an image of the specimen.

37. The system of claim 34, wherein the processor is further coupled to the inspection tool, wherein the processor is further configured to receive additional output from the inspection tool, wherein the additional output is responsive to the defects remaining on the specimen subsequent to the repair, and wherein the processor is further configured to alter a parameter of an instrument coupled to the repair tool in response to the additional output.

38. A system, comprising:
a wet cleaning chamber configured to process a specimen; and
a laser induced shock wave removal tool coupled to the wet cleaning chamber, wherein the removal tool is configured to remove particles from the specimen.

39. The system of claim 38, wherein the particles are located on frontside and backside surfaces of the specimen.

40. The system of claim 38, wherein the removal tool is further coupled to the wet cleaning chamber by a common handler.

41. The system of claim 38, further comprising a measurement device configured to detect defects present on the specimen.

42. The system of claim 41, further comprising a processor coupled to the measurement device and the removal tool, wherein the processor is configured to receive output from the measurement device, wherein the output is responsive to the defects detected on the specimen, and wherein the processor is further configured to alter a parameter of the removal tool in response to the output.

43. A system, comprising:
a wet cleaning chamber configured to process a specimen; and
a chemically assisted laser removal tool coupled to the wet cleaning chamber, wherein the removal tool is configured to remove particles from the specimen.

44. The system of claim 43, wherein the particles are located on frontside and backside surfaces of the specimen.

45. The system of claim 43, wherein the removal tool is further coupled to the wet cleaning chamber by a common handler.

46. The system of claim 43, further comprising a measurement device configured to detect defects present on the specimen.

47. The system of claim 46, further comprising a processor coupled to the measurement device and the removal tool, wherein the processor is configured to receive output from the measurement device, wherein the output is responsive to the defects detected on the specimen, and wherein the processor is further configured to alter a parameter of the removal tool in response to the output.

48. A system, comprising:
a cluster tool comprising at least one process chamber and a measurement device configured to detect defects present on a specimen; and
a cleaning chamber coupled to the cluster tool by a common handler, wherein the cleaning chamber is configured to process a single specimen.

49. The system of claim 48, further comprising a processor coupled to the measurement device and the at least one process chamber or the cleaning chamber, wherein the processor is configured to receive output from the measurement device, wherein the output is responsive to the defects detected on the specimen, and wherein the processor is further configured to alter a parameter of the at least one process chamber or the cleaning chamber in response to the output.

50. A system, comprising:
a measurement device configured to detect defects present on a specimen;
a processor coupled to the measurement device, wherein the processor is configured to analyze output from the measurement device to determine which of the defects are repairable by localized defect repair and which of the defects are repairable by processing the entire specimen; and
an inspection tool configured to detect defects remaining on the specimen subsequent to the localized defect repair or said processing the entire specimen;
wherein the processor is further configured to alter a parameter of an instrument coupled to a process chamber used to process the specimen in response to the defects remaining on the specimen subsequent to the repair.

51. The system of claim 50, wherein said processing the entire specimen comprises cleaning.

52. The system of claim 50, wherein the localized defect repair comprises removing the defects with chemically assisted laser removal, removing the defects with laser induced shock wave removal, or particle beam assisted repair.

53. The system of claim 50, wherein the processor is further configured to determine if the defects should be repaired or if the specimen should be further processed.

54. A method, comprising:
processing a specimen;
detecting defects present on the specimen subsequent to the processing;
analyzing the defects to determine if there is a problem with the processing and to determine which of the defects are repairable by localized defect repair and which of the defects are repairable by processing the entire specimen; and
if it is determined that there is a problem with the processing, altering a parameter of the processing prior to processing additional specimens.

55. The method of claim 54, wherein said analyzing comprises processing data responsive to the defects to determine if the defects are formed on the specimen due to individual process marginalities or by interactions of multiple processes.

56. The method of claim 54, wherein said analyzing comprises determining if characteristics, locations, numbers, or types of the defects are outside of a predetermined range.

* * * * *